United States Patent
Chen et al.

(10) Patent No.: US 11,259,726 B2
(45) Date of Patent: Mar. 1, 2022

(54) METHODS AND SYSTEMS FOR WEIGHTING CALIBRATION POINTS AND UPDATING LAG PARAMETERS

(71) Applicant: Senseonics, Incorporated, Germantown, MD (US)

(72) Inventors: Xiaoxiao Chen, Washington, DC (US); Ravi Rastogi, Columbia, MD (US); Andrew DeHennis, Germantown, MD (US); Patricia Sanchez, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 125 days.

(21) Appl. No.: 16/142,711

(22) Filed: Sep. 26, 2018

(65) Prior Publication Data
US 2019/0090790 A1 Mar. 28, 2019

Related U.S. Application Data

(60) Provisional application No. 62/649,329, filed on Mar. 28, 2018, provisional application No. 62/566,846, (Continued)

(51) Int. Cl.
*A61B 5/145* (2006.01)
*A61B 5/1495* (2006.01)
(Continued)

(52) U.S. Cl.
CPC .......... *A61B 5/1495* (2013.01); *A61B 5/1451* (2013.01); *A61B 5/1459* (2013.01);
(Continued)

(58) Field of Classification Search
CPC ... A61B 5/1495; A61B 5/1459; A61B 5/1451; A61B 5/14532; A61B 5/742;
(Continued)

(56) References Cited

U.S. PATENT DOCUMENTS

| | | | |
|---|---|---|---|
| 6,088,608 | A | 7/2000 | Schulman et al. |
| 6,895,263 | B2 | 5/2005 | Shin et al. |

(Continued)

FOREIGN PATENT DOCUMENTS

| | | |
|---|---|---|
| EP | 1518495 B1 | 3/2010 |
| EP | 2335584 A2 | 6/2011 |

(Continued)

*Primary Examiner* — Eric F Winakur
(74) *Attorney, Agent, or Firm* — Rothwell, Figg, Ernst & Manbeck, P.C.

(57) ABSTRACT

Disclosed are analyte monitoring systems and methods for calibrating an analyte sensor using one or more reference measurements. These systems and methods may include using a conversion function and first sensor data to calculate a first sensor analyte level, weighting a first reference analyte measurement (RM1) and one or more previous reference analyte measurements according to a weighted average cost function, updating the conversion function using the weighted RM1 and the one or more weighted previous reference analyte measurements as calibration points, and using the updated conversion function and second sensor data to calculate a second sensor analyte level. In some aspects, the systems and methods may include updating one or more of lag parameters used to calculate the sensor analyte levels.

34 Claims, 9 Drawing Sheets

Related U.S. Application Data filed on Oct. 2, 2017, provisional application No. 62/563,240, filed on Sep. 26, 2017.

(51) Int. Cl.
*A61B 5/1459* (2006.01)
*A61B 5/00* (2006.01)
*G01N 33/66* (2006.01)

(52) U.S. Cl.
CPC .......... *A61B 5/14532* (2013.01); *A61B 5/742* (2013.01); *G01N 33/66* (2013.01); *A61B 5/14503* (2013.01); *A61B 5/4866* (2013.01); *A61B 2560/0223* (2013.01)

(58) Field of Classification Search
CPC . A61B 5/14503; A61B 5/7275; A61B 5/7203; A61B 5/7235
See application file for complete search history.

(56) References Cited

U.S. PATENT DOCUMENTS

| | | |
|---|---|---|
| 7,389,133 B1 | 6/2008 | Kotulla et al. |
| 7,920,906 B2 | 4/2011 | Goode, Jr. et al. |
| 8,073,548 B2 | 12/2011 | Colvin, Jr. et al. |
| 8,282,550 B2 | 10/2012 | Rasdal et al. |
| 8,394,021 B2 | 3/2013 | Goode et al. |
| 9,220,449 B2 | 12/2015 | Pryor et al. |
| 9,414,775 B2 | 8/2016 | Colvin, Jr. et al. |
| 9,557,582 B2 | 1/2017 | Honore et al. |
| 9,571,578 B1 | 2/2017 | Andre et al. |
| 9,629,578 B2 | 4/2017 | Hayter et al. |
| 9,662,056 B2 | 5/2017 | Budiman et al. |
| 9,693,714 B2 | 7/2017 | DeHennis et al. |
| 9,788,354 B2 | 10/2017 | Miller et al. |
| 9,804,148 B2 | 10/2017 | Hayter et al. |
| 10,028,686 B2 | 7/2018 | Hayter |
| 2008/0081977 A1 | 4/2008 | Hayter et al. |
| 2008/0314395 A1 | 12/2008 | Kovatchev et al. |
| 2009/0054748 A1 | 2/2009 | Feldman |
| 2010/0185073 A1 | 7/2010 | Goode, Jr. et al. |
| 2011/0237917 A1 | 9/2011 | Roy et al. |
| 2012/0108931 A1 | 5/2012 | Taub et al. |
| 2013/0102866 A1 | 4/2013 | Li et al. |
| 2013/0241745 A1 | 9/2013 | Colvin, Jr. et al. |
| 2014/0345584 A1 | 11/2014 | Jammoussi et al. |
| 2015/0182115 A1 | 7/2015 | DeHennis |
| 2015/0216456 A1* | 8/2015 | Budiman .............. A61B 5/7235 600/309 |
| 2016/0245791 A1 | 8/2016 | Hayter et al. |
| 2016/0270740 A1 | 9/2016 | Raisoni et al. |

FOREIGN PATENT DOCUMENTS

| | | |
|---|---|---|
| EP | 2497420 A1 | 9/2012 |
| EP | 2329770 B1 | 9/2014 |
| EP | 2329763 B1 | 6/2017 |
| EP | 2770907 B1 | 7/2018 |
| WO | 03/094714 A1 | 11/2003 |
| WO | 2013/033357 A1 | 3/2013 |

* cited by examiner

METHODS AND SYSTEMS FOR WEIGHTING CALIBRATION POINTS AND UPDATING LAG PARAMETERS

CROSS-REFERENCE TO RELATED APPLICATIONS

The present application claims the benefit of priority to U.S. Provisional Application Ser. No. 62/649,329, filed on Mar. 28, 2018, U.S. Provisional Application Ser. No. 62/566,846, filed on Oct. 2, 2017, and U.S. Provisional Application Ser. No. 62/563,240, filed on Sep. 26, 2017, each of which is incorporated herein by reference in their entireties.

BACKGROUND

Field of Invention

The present invention relates to calibrating an analyte sensor of an analyte monitoring system used to calculate analyte levels in a first medium using at least one measurement from a second medium. More specifically, aspects of the present invention relate to weighting calibration points and updating lag parameters at different time periods. Even more specifically, aspects of the present invention relate to calculating blood analyte levels using measurements of interstitial fluid analyte levels and one or more of weighted calibration points and different lag parameters for different time periods.

Discussion of the Background

Analyte monitoring systems may be used to measure analyte levels, such as analyte amounts or concentrations. One type of analyte monitoring system is a continuous glucose monitoring (CGM) system. A CGM system measures glucose levels throughout the day and can be very useful in the management of diabetes. Some analyte monitoring systems use measurements indicative of analyte levels in interstitial fluid ("ISF") to calculate ISF analyte levels and then convert the ISF analyte levels to blood analyte levels. The analyte monitoring systems may display the blood analyte levels to a user. However, because ISF analyte levels lag behind blood analyte levels, accurate conversion of ISF analyte levels to blood analyte levels is difficult.

Analyte monitoring systems require calibration (and re-calibration) to maintain accuracy and sensitivity. The calibration may be, for example and without limitation, performed daily or twice-daily. The calibration may be performed using one or more reference measurements. The reference measurements may be, for example and without limitation, self-monitoring blood glucose (SMBG) measurements. The reference measurements may be, for example and without limitation, obtained from finger-stick blood samples.

Improved calibration systems and methods are needed for more accurate analyte monitoring.

SUMMARY

Aspects of the present invention relate to improving calibration reliability and analyte measurement accuracy by mitigating the errors in historical calibration points and/or to avoid over-fitting the current calibration point based on recent calibration points. Aspects of the present invention relate to assigning weights to one or more historical calibration points in order to avoid over-fitting the calibration point based on recent readings and thereby increasing sensor measurement accuracy. The improvement in sensor measurement accuracy may, for example and without limitation, limit the number of false alerts related to high or low analyte levels, which may be especially helpful overnight when a user is trying to sleep.

Aspects of the present invention involve updating one or more parameters used to calculate an analyte level in a first medium using an analyte level in a second medium. In some embodiments, these parameters may be lag parameters that model, for example, diffusion and consumption rates of an analyte. Updating the lag parameters over time may lead to increased sensor accuracy because the lag time may change over the life cycle of the sensor. An aspect of the present invention involves determining whether to update these parameters, for example, based on whether a period of time has passed since the lag parameters were last updated.

One aspect of the invention provides a method of calibrating an analyte sensor using one or more reference measurements. The method may include receiving first sensor data from an analyte sensor. The method may include using a conversion function and the first sensor data to calculate a first sensor analyte level. The method may include receiving a first reference analyte measurement (RM1). The method may include storing the RM1 in a calibration point memory that includes one or more previous reference analyte measurements. The method may include weighting the RM1 and the one or more previous reference analyte measurements according to a weighted average cost function. The method may include updating the conversion function using the weighted RM1 and the one or more weighted previous reference analyte measurements as calibration points. The method may include receiving second sensor data from the analyte sensor. The method may include using the updated conversion function and the second sensor data to calculate a second sensor analyte level.

In some embodiments, the RM1 may be a self-monitoring blood glucose (SMBG) measurement obtained from a finger-stick blood sample. In some embodiments, the calibration point memory may be a circular buffer.

In some embodiments, the weightings for the weighted RM1 and the one or more weighted previous reference analyte measurements may be calculated using an exponential growth formula. In some embodiments, the exponential growth formula may include a growth parameter $\alpha$ defined as $$\alpha = \left(\frac{t_i - t_0}{\lambda}\right),$$

$t_0$ may be the time stamp of the current calibration point, i may equal $-(N-1), -(N-2), \ldots 0$, N may be the number of calibration points, and $\lambda$, may be the relative time difference between the current and the previous calibration points. In some embodiments, N may be a constant value. In some embodiments, $\lambda$, may be a constant value.

In some embodiments, the weighted average cost function may include an accuracy metric, $\text{Error}(\theta)_i$.

In some embodiments, the calculated first sensor analyte level may be a level of analyte in a first medium, and the first sensor data may comprise one or more measurements of an analyte level in a second medium. In some embodiments, the first medium may be blood, and the second medium may be interstitial fluid. In some embodiments, using the conversion function and the first sensor data used to calculate the first sensor analyte measurement may include: calculating a second medium analyte level using at least the first sensor data, calculating a second medium level rate of change using at least the second medium analyte level, and calculating the first sensor analyte level using at least the second medium analyte level and the second medium level rate of change. In some embodiments, the first sensor analyte level may be calculated using at least the second medium analyte level, the second medium level rate of change, and one or more lag parameters. In some embodiments, the one or more lag parameters may include one or more of an analyte diffusion rate and an analyte consumption rate.

In some embodiments, the method may further include determining whether to update one or more of the lag parameters. In some embodiments, the method may further include updating one or more of the lag parameters. In some embodiments, determining whether to update one or more of the lag parameters may include determining whether a period of time has passed since the one or more of the lag parameters has been updated.

In some embodiments, the method may further include updating one or more of the lag parameters. In some embodiments, updating one or more lag parameters may include using one or more of a first method and a second method to estimate one or more updated lag parameters. In some embodiments, the first method may be a ratio method. In some embodiments, the second method may be a two-parameter method. In some embodiments, updating one or more lag parameters may include using the first method during a first period and using the second method during a second period. In some embodiments, updating one or more lag parameters may include using both the first and second methods. In some embodiments, using both the first and second methods may include using the first method to estimate a first set of updated lag parameters. In some embodiments, using both the first and second methods may include using the second method to estimate a second set of updated lag parameters. In some embodiments, using both the first and second methods may include using the first set of updated lag parameters to calculate one or more first sensor measurements. In some embodiments, using both the first and second methods may include using the second set of updated lag parameters to calculate one or more second sensor measurements. In some embodiments, using both the first and second methods may include evaluating the one or more first sensor measurements and the one or more second sensor measurements by comparing the one or more first sensor measurements and the one or more second sensor measurements to one or more reference measurements. In some embodiments, using both the first and second methods may include selecting the more accurate of (a) the one or more first sensor measurements and (b) the one or more second sensor measurements for display to a user.

In some embodiments, the first sensor analyte level may be calculated using a two-compartment model that models the transport of the analyte from the first medium and in the second medium. In some embodiments, the two-compartment model may be $$\frac{dC_2}{dt} = p_2 * [C_1(t) - C_2(t)] - p_3 * C_2(t),$$

where $C_1(t)$ may be a concentration of the analyte in the first medium, $C_2(t)$ may be a concentration of the analyte in the second medium, p2 may be an analyte diffusion rate, and p3 may be an analyte consumption rate. In some embodiments, $1/p_2$ and $p_3/p_2$ may be lag parameters.

In some embodiments, the method may further include determining whether to dynamically update one or more of the lag parameters. In some embodiments, the method may further include dynamically updating one or more of the lag parameters. In some embodiments, dynamically updating one or more of the lag parameters may include using a minimum deviation divergence method.

In some embodiments, the conversion function may employ an asymmetrical lag methodology. In some embodiments, the asymmetrical lag approach may decelerate a rate of change of falling glucose levels during a low blood glucose event and accelerates a rate of change of increasing glucose levels during recovery from the low blood glucose event.

Another aspect of the invention provides an analyte monitoring system including an analyte sensor and a transceiver. The analyte sensor may include an indicator element that exhibits one or more detectable properties based on a concentration of an analyte in proximity to the indicator element. The transceiver may be configured to receive first sensor data from the analyte sensor. The transceiver may be configured to use a conversion function and the first sensor data to calculate a first sensor analyte level. The transceiver may be configured to receive a first reference analyte measurement (RM1). The transceiver may be configured to store the RMI in a calibration point memory that includes one or more previous reference analyte measurements. The transceiver may be configured to weight the RM1 and the one or more previous reference analyte measurements according to a weighted average cost function. The transceiver may be configured to update the conversion function using the weighted RM1 and the one or more weighted previous reference analyte measurements as calibration points. The transceiver may be configured to receive second sensor data from the analyte sensor. The transceiver may be configured to use the updated conversion function and the second sensor data to calculate a second sensor analyte level.

In some embodiments, the RM1 may be a self-monitoring blood glucose (SMBG) measurement obtained from a finger-stick blood sample. In some embodiments, the calibration point memory may be a circular buffer.

In some embodiments, the weightings for the weighted RM1 and the one or more weighted previous reference analyte measurements may be calculated using an exponential growth formula. In some embodiments, the exponential growth formula may include a growth parameter α defined as $$\alpha = \left(\frac{t_i - t_0}{\lambda}\right),$$

$t_0$ may be the time stamp of the current calibration point, i may equal $-(N-1), -(N-2), \ldots 0$, N may be the number of calibration points, and λ may be the relative time difference between the current and the previous calibration points. In some embodiments, N may be a constant value. In some embodiments, λ may be a constant value.

In some embodiments, the weighted average cost function may include an accuracy metric, $Error(\theta)_i$. In some embodiments, the calculated first sensor analyte level may be a level of the analyte in a first medium, and the first sensor data may include one or more measurements of the analyte level in a second medium. In some embodiments, the first medium may be blood, and the second medium may be interstitial fluid.

In some embodiments, the transceiver may be further configured to: calculate a second medium analyte level using at least the first sensor data, calculate a second medium level rate of change using at least the second medium analyte level, and calculate the first sensor analyte level using at least the second medium analyte level and the second medium level rate of change. In some embodiments, the first sensor analyte level may be calculated using at least the second medium analyte level, the second medium level rate of change, and one or more lag parameters. In some embodiments, the one or more lag parameters may include one or more of an analyte diffusion rate and an analyte consumption rate. In some embodiments, the transceiver may be further configured to determine whether to update one or more of the lag parameters. In some embodiments, the transceiver may be further configured to update one or more of the lag parameters. In some embodiments, determining whether to update one or more of the lag parameters may include determining whether a period of time has passed since the one or more of the lag parameters has been updated.

In some embodiments, the transceiver may be further configured to update one or more of the lag parameters. In some embodiments, updating one or more lag parameters may include using one or more of a first method and a second method to estimate one or more updated lag parameters. In some embodiments, the first method may be a ratio method. In some embodiments, the second method may be a two-parameter method. In some embodiments, updating one or more lag parameters may include using the first method during a first period and using the second method during a second period. In some embodiments, updating one or more lag parameters may include using both the first and second methods. In some embodiments, using both the first and second methods may include one or more of: using the first method to estimate a first set of updated lag parameters; using the second method to estimate a second set of updated lag parameters; using the first set of updated lag parameters to calculate one or more first sensor measurements; using the second set of updated lag parameters to calculate one or more second sensor measurements; evaluating the one or more first sensor measurements and the one or more second sensor measurements by comparing the one or more first sensor measurements and the one or more second sensor measurements to one or more reference measurements; and selecting the more accurate of (a) the one or more first sensor measurements and (b) the one or more second sensor measurements for display to a user.

In some embodiments, the first sensor analyte level may be calculated using a two-compartment model that models the transport of the analyte from the first medium and in the second medium. In some embodiments, the two-compartment model may be $$\frac{dC_2}{dt} = p_2 * [C_1(t) - C_2(t)] - p_3 * C_2(t),$$

$C_1(t)$ may be a concentration of the analyte in the first medium, $C_2(t)$ may be a concentration of the analyte in the second medium, $p2$ may be an analyte diffusion rate, and $p3$ may be an analyte consumption rate. In some embodiments, $1/p_2$ and $p_3/p_2$ may be lag parameters.

In some embodiments, the transceiver may be further configured to determine whether to dynamically update one or more of the lag parameters. In some embodiments, the transceiver may be further configured to dynamically update one or more of the lag parameters. In some embodiments, dynamically updating one or more of the lag parameters may include using a minimum deviation divergence method.

In some embodiments, the conversion function may employ an asymmetrical lag methodology. In some embodiments, the asymmetrical lag approach may decelerate a rate of change of falling glucose levels during a low blood glucose event and accelerate a rate of change of increasing glucose levels during recovery from the low blood glucose event.

Still another aspect of the invention provides a method of calculating an analyte level in a first medium using one or more measurements of an analyte level in a second medium. The method may include receiving first sensor data from an analyte sensor. The method may include calculating a first analyte level in the second medium using at least the first sensor data. The method may include calculating a first analyte level rate of change using at least the first analyte level in the second medium. The method may include calculating a first analyte level in the first medium using at least the first analyte level in the second medium, the first analyte level rate of change, and one or more lag parameters. The method may include determining that the one or more lag parameters should be updated. The method may include updating the one or more lag parameters. The method may include receiving second sensor data from the analyte sensor. The method may include calculating a second analyte level in the second medium using at least the second sensor data. The method may include calculating a second analyte level rate of change using at least the second analyte level in the second medium. The method may include calculating a second analyte level in the first medium using at least the second analyte level in the second medium, the second analyte level rate of change, and the updated one or more lag parameters.

In some embodiments, the one or more lag parameters may include one or more of an analyte diffusion rate and an analyte consumption rate. In some embodiments, determining that the one or more lag parameters should be updated may include determining that a period of time has passed since the one or more of the lag parameters has been updated. In some embodiments, the first medium may be blood, and the second medium may be interstitial fluid.

In some embodiments, the method may further include determining whether to dynamically update one or more of the lag parameters. In some embodiments, the method may further include dynamically updating one or more of the lag parameters. In some embodiments, dynamically updating one or more of the lag parameters may include using a minimum deviation divergence method.

In some embodiments, calculating the first analyte level in the first medium may include employing an asymmetrical lag methodology. In some embodiments, the asymmetrical lag approach may decelerate a rate of change of falling glucose levels during a low blood glucose event and accelerate a rate of change of increasing glucose levels during recovery from the low blood glucose event.

In some embodiments, updating one or more lag parameters may include using one or more of a first method and a second method to estimate one or more updated lag parameters. In some embodiments, the first method may be a ratio method. In some embodiments, the second method may be a two-parameter method. In some embodiments, updating one or more lag parameters may include using the first method during a first period and using the second method during a second period. In some embodiments, updating one or more lag parameters may include using both the first and second methods. In some embodiments, using both the first and second methods may include one or more of: using the first method to estimate a first set of updated lag parameters; using the second method to estimate a second set of updated lag parameters; using the first set of updated lag parameters to calculate one or more first sensor measurements; using the second set of updated lag parameters to calculate one or more second sensor measurements; evaluating the one or more first sensor measurements and the one or more second sensor measurements by comparing the one or more first sensor measurements and the one or more second sensor measurements to one or more reference measurements; and selecting the more accurate of (a) the one or more first sensor measurements and (b) the one or more second sensor measurements for display to a user.

Yet another aspect of the invention provides an analyte monitoring system including an analyte sensor and a transceiver. The analyte sensor may include an indicator element that exhibits one or more detectable properties based on a concentration of an analyte in proximity to the indicator element. The transceiver may be configured to receive first sensor data from the analyte sensor. The transceiver may be configured to calculate a first analyte level in the second medium using at least the first sensor data. The transceiver may be configured to calculate a first analyte level rate of change using at least the first analyte level in the second medium. The transceiver may be configured to calculate a first analyte level in the first medium using at least the first analyte level in the second medium, the first analyte level rate of change, and one or more lag parameters. The transceiver may be configured to determine that the one or more lag parameters should be updated. The transceiver may be configured to update the one or more lag parameters. The transceiver may be configured to receive second sensor data from the analyte sensor. The transceiver may be configured to calculate a second analyte level in the second medium using at least the second sensor data. The transceiver may be configured to calculate a second analyte level rate of change using at least the second analyte level in the second medium. The transceiver may be configured to calculate a second analyte level in the first medium using at least the second analyte level in the second medium, the second analyte level rate of change, and the updated one or more lag parameters.

In some embodiments, the one or more lag parameters may include one or more of an analyte diffusion rate and an analyte consumption rate. In some embodiments, determining that the one or more lag parameters should be updated may include determining that a period of time has passed since the one or more of the lag parameters has been updated. In some embodiments, the first medium may be blood, and the second medium may be interstitial fluid.

In some embodiments, the transceiver may be further configured to determine whether to dynamically update one or more of the lag parameters. In some embodiments, the transceiver may be further configured to dynamically update one or more of the lag parameters. In some embodiments, dynamically updating one or more of the lag parameters may include using a minimum deviation divergence method.

In some embodiments, the transceiver may be further configured to dynamically update one or more of the lag parameters. In some embodiments, calculating the first analyte level in the first medium may include employing an asymmetrical lag methodology. In some embodiments, the asymmetrical lag approach may decelerate a rate of change of falling glucose levels during a low blood glucose event and accelerate a rate of change of increasing glucose levels during recovery from the low blood glucose event.

In some embodiments, updating one or more lag parameters may include using one or more of a first method and a second method to estimate one or more updated lag parameters. In some embodiments, the first method may be a ratio method. In some embodiments, the second method may be a two-parameter method. In some embodiments, updating one or more lag parameters may include using the first method during a first period and using the second method during a second period. In some embodiments, updating one or more lag parameters may include using both the first and second methods. In some embodiments, using both the first and second methods may include one or more of: using the first method to estimate a first set of updated lag parameters; using the second method to estimate a second set of updated lag parameters; using the first set of updated lag parameters to calculate one or more first sensor measurements; using the second set of updated lag parameters to calculate one or more second sensor measurements; evaluating the one or more first sensor measurements and the one or more second sensor measurements by comparing the one or more first sensor measurements and the one or more second sensor measurements to one or more reference measurements; and selecting the more accurate of (a) the one or more first sensor measurements and (b) the one or more second sensor measurements for display to a user.

Another aspect of the invention may provide a method of calculating an analyte level in a first medium using one or more measurements of an analyte level in a second medium. The method may include receiving first sensor data from an analyte sensor. The method may include calculating a first analyte level in the second medium using at least the first sensor data. The method may include calculating a first analyte level rate of change using at least the first analyte level in the second medium. The method may include calculating a first analyte level in the first medium using at least the first analyte level in the second medium, the first analyte level rate of change, and a first set of one or more lag parameters. The method may include calculating a second analyte level in the first medium using at least the first analyte level in the second medium, the first analyte level rate of change, and a second set of one or more lag parameters. The method may include comparing the first analyte level in the first medium to at least a reference measurement. The method may include comparing the second analyte level in the first medium to at least the reference measurement. The method may include selecting whichever of the first analyte level in the first medium and the second analyte level in the first medium is closer to the reference measurement for display to a user.

Another aspect of the invention may provide an analyte sensor and a transceiver. The analyte sensor may include an indicator element that exhibits one or more detectable properties based on a concentration of an analyte in proximity to the indicator element. The transceiver may be configured to receive first sensor data from the analyte sensor. The transceiver may be configured to calculate a first analyte level in the second medium using at least the first sensor data. The transceiver may be configured to calculate a first analyte level rate of change using at least the first analyte level in the second medium. The transceiver may be configured to calculate a first analyte level in the first medium using at least the first analyte level in the second medium, the first analyte level rate of change, and a first set of one or more lag parameters. The transceiver may be configured to calculate a second analyte level in the first medium using at least the first analyte level in the second medium, the first analyte level rate of change, and a second set of one or more lag parameters. The transceiver may be configured to compare the first analyte level in the first medium to at least a reference measurement. The transceiver may be configured to compare the second analyte level in the first medium to at least the reference measurement. The transceiver may be configured to select whichever of the first analyte level in the first medium and the second analyte level in the first medium is closer to the reference measurement for display to a user.

Another aspect of the invention may provide a method including receiving first sensor data from an analyte sensor. The method may include using a conversion function and at least the first sensor data to calculate a first sensor analyte level. The method may include receiving second sensor data from the analyte sensor. The method may include using the conversion function and at least the second sensor data to calculate a second sensor analyte level. The method may include receiving a first reference analyte measurement (RM1). The RM1 may have a time stamp in between time stamps of the first and second sensor analyte levels. The method may include updating the conversion function using at least the RM1 as a calibration point. Updating the conversion function may include interpolating a sensor analyte level having a time stamp that matches the time stamp of the RM1 using at least the first and second sensor analyte levels and the time stamps of the first and second sensor analyte levels. Updating the conversion function may include pairing the RM1 with the interpolated sensor analyte level. Updating the conversion function may include using the pairing of the RM1 with the interpolated sensor analyte value to update the conversion function. The method may include receiving third sensor data from the analyte sensor. The method may include using the updated conversion function to calculate a third sensor analyte level.

In some embodiments, interpolating the sensor analyte level having the time stamp that matches the time stamp of the RM1 may use linear interpolation. In some embodiments, interpolating the sensor analyte level having the time stamp that matches the time stamp of the RM1 may use polynomial interpolation. In some embodiments, interpolating the sensor analyte level having the time stamp that matches the time stamp of the RM1 may use spline interpolation. In some embodiments, the RM1 may be a self-monitoring blood glucose (SMBG) measurement obtained from a finger-stick blood sample.

In some embodiments, the conversion function may employ an asymmetrical lag methodology. In some embodiments, the asymmetrical lag approach may decelerate a rate of change of falling glucose levels during a low blood glucose event and accelerate a rate of change of increasing glucose levels during recovery from the low blood glucose event.

Yet another aspect of the invention may provide an analyte monitoring system including an analyte sensor and a transceiver. The analyte sensor may include an indicator element that exhibits one or more detectable properties based on a concentration of an analyte in proximity to the indicator element. The transceiver may be configured to receive first sensor data from the analyte sensor. The transceiver may be configured to use a conversion function and at least the first sensor data to calculate a first sensor analyte level. The transceiver may be configured to receive second sensor data from the analyte sensor. The transceiver may be configured to use the conversion function and at least the second sensor data to calculate a second sensor analyte level. The transceiver may be configured to receive a first reference analyte measurement (RM1). The RM1 may have a time stamp in between time stamps of the first and second sensor analyte levels. The transceiver may be configured to update the conversion function using at least the RM1 as a calibration point. Updating the conversion function may include interpolating a sensor analyte level having a time stamp that matches the time stamp of the RM1 using at least the first and second sensor analyte levels and the time stamps of the first and second sensor analyte levels. Updating the conversion function may include pairing the RM1 with the interpolated sensor analyte level. Updating the conversion function may include using the pairing of the RM1 with the interpolated sensor analyte value to update the conversion function. The transceiver may be configured to receive third sensor data from the analyte sensor. The transceiver may be configured to use the updated conversion function to calculate a third sensor analyte level.

In some embodiments, the transceiver may be configured to interpolate the sensor analyte level having the time stamp that matches the time stamp of the RM1 using linear interpolation. In some embodiments, the transceiver may be configured to interpolate the sensor analyte level having the time stamp that matches the time stamp of the RM1 using polynomial interpolation. In some embodiments, the transceiver may be configured to interpolate the sensor analyte level having the time stamp that matches the time stamp of the RM1 using spline interpolation. In some embodiments, the RM1 may be a self-monitoring blood glucose (SMBG) measurement obtained from a finger-stick blood sample.

In some embodiments, the conversion function may employ an asymmetrical lag methodology. In some embodiments, the asymmetrical lag approach may decelerate a rate of change of falling glucose levels during a low blood glucose event and accelerate a rate of change of increasing glucose levels during recovery from the low blood glucose event.

Still another aspect of the invention may provide a method including using a display device to prompt a user to enter a reference measurement. The method may include using the display device to receive a reference measurement. The method may include using the display device to prompt a user to enter a time at which the reference measurement was taken. The method may include using the display device to receive a time at which the reference measurement was taken. The method may include using the display device to display an analyte level.

In some embodiments, the reference measurement may be a self-monitoring blood glucose (SMBG) measurement obtained from a finger-stick blood sample.

In some embodiments, the method may further include using the display device to convey the received reference measurement and the received time to a transceiver and may include using the display device to receive the analyte level from the transceiver. In some embodiments, the method may further include one or more of: using the transceiver to receive sensor data from an analyte sensor; using the transceiver to calculate the analyte level using a conversion function and the sensor data; and using the transceiver to convey the analyte level to the display device. In some embodiments, the method may further include one or more of: using the transceiver to receive the reference measurement and the time at which the reference measurement was taken; and using the transceiver to update the conversion function using the reference measurement and the time at which the reference measurement was taken. In some embodiments, the method may further include storing the reference measurement in a calibration point memory. In some embodiments, the sensor data may be first sensor data, the analyte level may be a first analyte level, and the method further include one or more of: using the transceiver to receive second sensor data from the analyte sensor; using the transceiver to calculate a second sensor analyte level using the updated conversion function and the second sensor data; and using the transceiver to convey the second analyte level to the display device. In some embodiments, the method may further include using the display device to receive the second analyte level from the transceiver and using the display device to display the second analyte level.

Yet another aspect of the invention may provide an analyte monitoring system include a transceiver and a display device. The transceiver may be configured to convey an analyte level. The display device may be configured to: prompt a user to enter a reference measurement, receive a reference measurement, prompt a user to enter a time at which the reference measurement was taken, receive a time at which the reference measurement was taken, receive the analyte level from the transceiver, and display the analyte level.

In some embodiments, the reference measurement may be a self-monitoring blood glucose (SHBG) measurement obtained from a finger-stick blood sample.

In some embodiments, the display device may be further configured to convey the received reference measurement and the received time to the transceiver. In some embodiments, the analyte monitoring system may further include an analyte sensor, and the transceiver may be further configured to: receive sensor data from the analyte sensor, calculate the analyte level using a conversion function and the sensor data, and convey the analyte level to the display device. In some embodiments, the transceiver may be further configured to: receive the reference measurement and the time at which the reference measurement was taken from the display device, and update the conversion function using the reference measurement and the time at which the reference measurement was taken. In some embodiments, the transceiver may be further configured to store the reference measurement in a calibration point memory. In some embodiments, the sensor data may be first sensor data, the analyte level may be a first analyte level, and the transceiver may be further configured to: receive second sensor data from the analyte sensor, calculate a second sensor analyte level using the updated conversion function and the second sensor data, and convey the second analyte level to the display device. In some embodiments, the display device may be further configured to: receive the second analyte level from the transceiver, and display the second analyte level.

Another aspect of the invention may provide a display device including a transceiver interface, a user interface, and a computer. The transceiver interface may be configured to receive an analyte level from a transceiver. The computer may include a non-transitory memory and a processor. The computer may be configured to (i) cause the user interface to display the analyte level, (ii) cause the user interface to prompt a user to enter a reference measurement, (iii) receive a reference measurement entered using the user interface, (iv) cause the user interface to prompt a user to enter a time at which the reference measurement was taken, and (v) receive a time at which the reference measurement was taken. The received time may have been entered using the user interface.

In some embodiments, the reference measurement may be a self-monitoring blood glucose (SHBG) measurement obtained from a finger-stick blood sample. In some embodiments, the computer may be further configured to cause the transceiver interface to convey the received reference measurement and the received time to the transceiver. In some embodiments, the transceiver interface may include an antenna.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
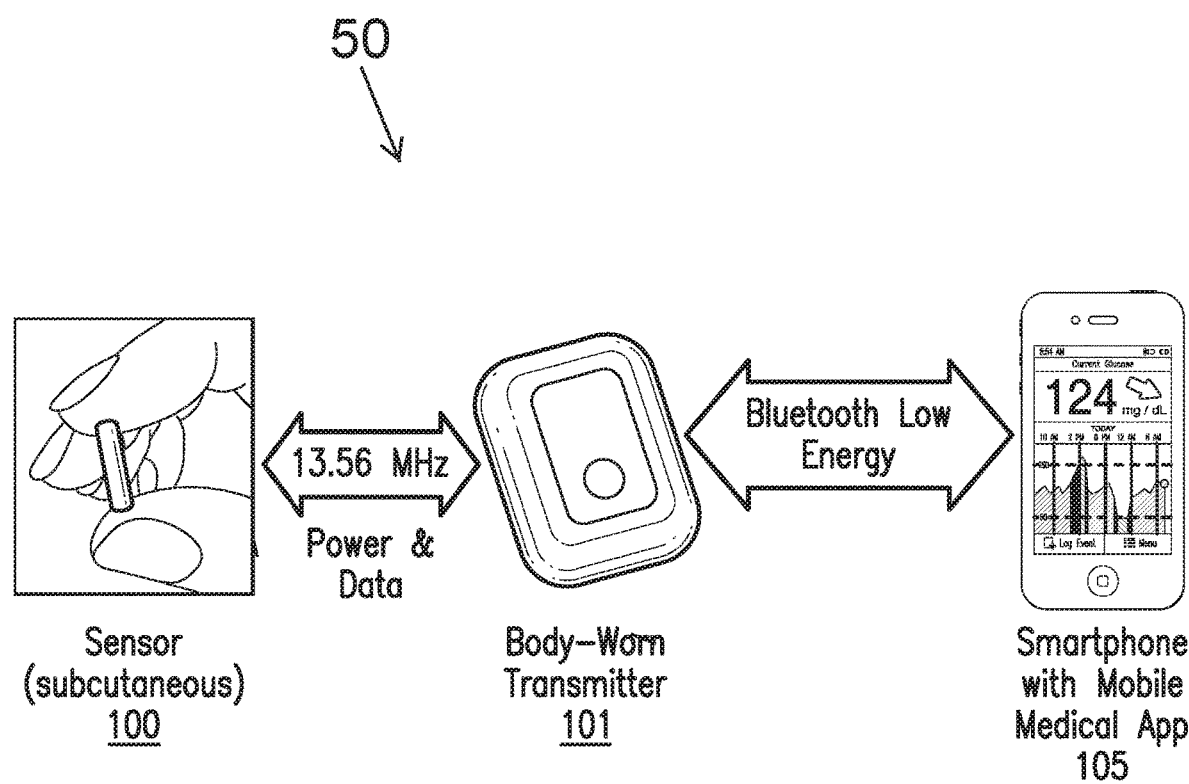
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and a display device 105. In some embodiments, the sensor 100 may be small, fully subcutaneously implantable sensor that measures analyte (e.g., glucose) levels in a medium (e.g., interstitial fluid) of a living animal (e.g., a living human). However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte levels) wirelessly (e.g., via a Bluetooth™ communication standard such as, for example and without limitation Bluetooth Low Energy) to a hand held application running on a display device 105 (e.g., smartphone). In some embodiments, the analyte monitoring system 50 may include a web interface for plotting and sharing of uploaded data.

Figure 2:
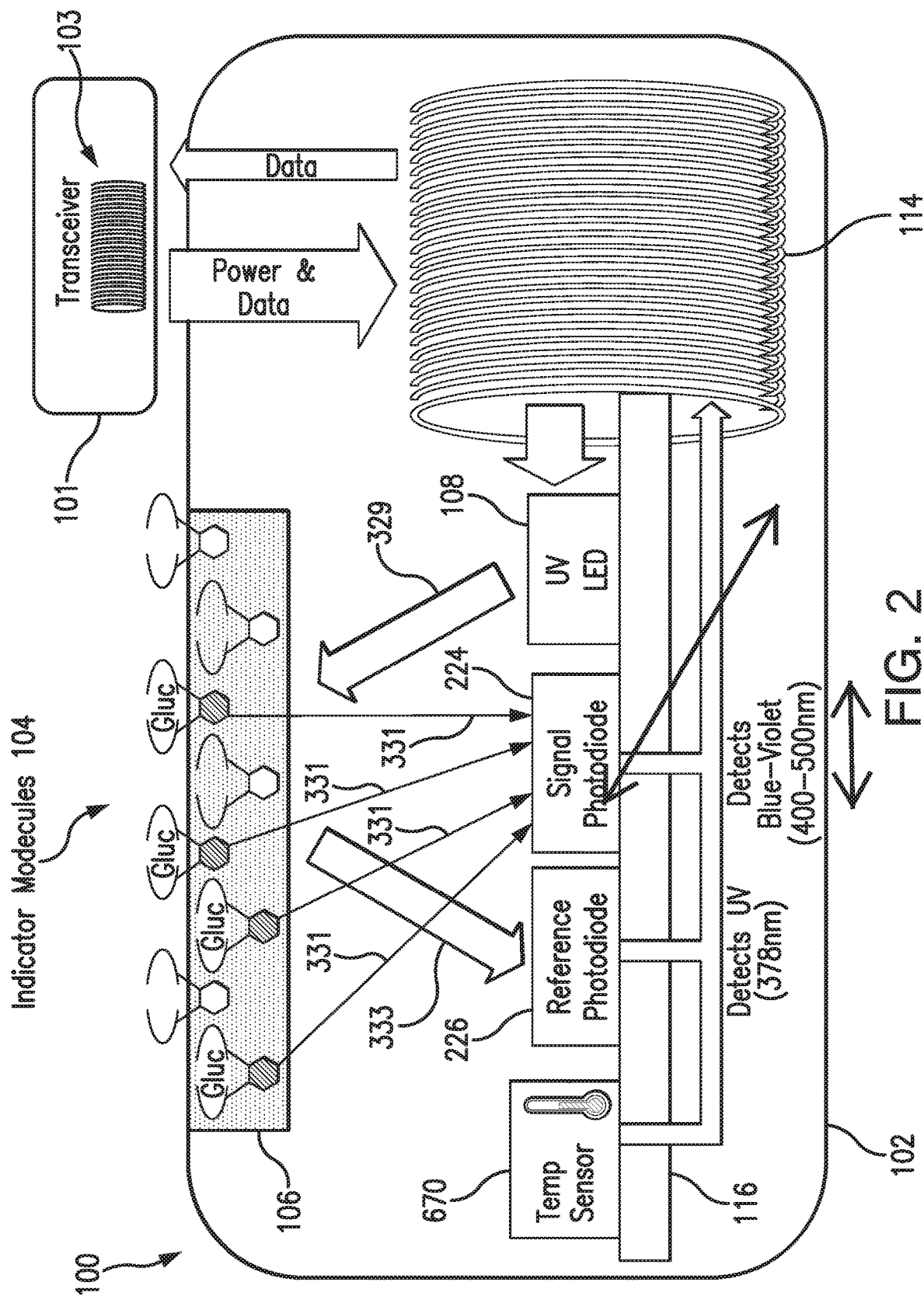
FIG. 2 is a schematic view illustrating a sensor and transceiver of an analyte monitoring system embodying aspects of the present invention.

In some embodiments, as illustrated in FIG. 2, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive sensor data (e.g., measurement information) from the sensor 100. For example, in a non-limiting embodiment, the transceiver 101 may receive sensor data by detecting modulations in the electromagnetic wave generated by the sensor 100, (e.g., by detecting modulations in the current flowing through the coil 103 of the transceiver 101).

The inductive element 103 of the transceiver 101 and the inductive element 114 of the sensor 100 may be in any configuration that permits adequate field strength to be achieved when the two inductive elements are brought within adequate physical proximity.

In some non-limiting embodiments, as illustrated in FIG. 2, the sensor 100 may be encased in a sensor housing 102 (e.g., body, shell, capsule, or encasement), which may be rigid and biocompatible. The sensor 100 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto is indicative of the level of emission light 331 of the indicator molecules and, thus, the amount or concentration of the analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductive element 114), the transceiver interface device may include the antenna (e.g., inductive element 114) of sensor 100. In some of the transcutaneous embodiments where there exists a wired connection between the sensor 100 and the transceiver 101, the transceiver interface device may include the wired connection.

Figure 3:
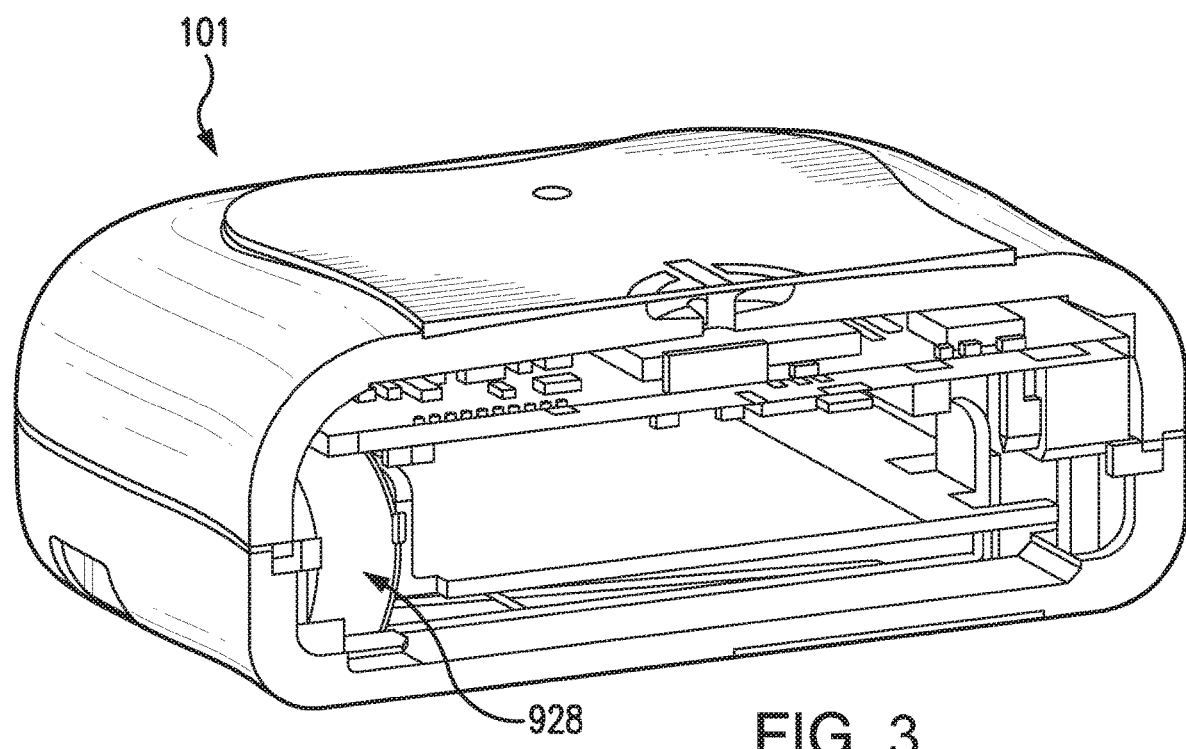
FIG. 3 is cross-sectional, perspective view of a transceiver embodying aspects of the invention.
Figure 4:
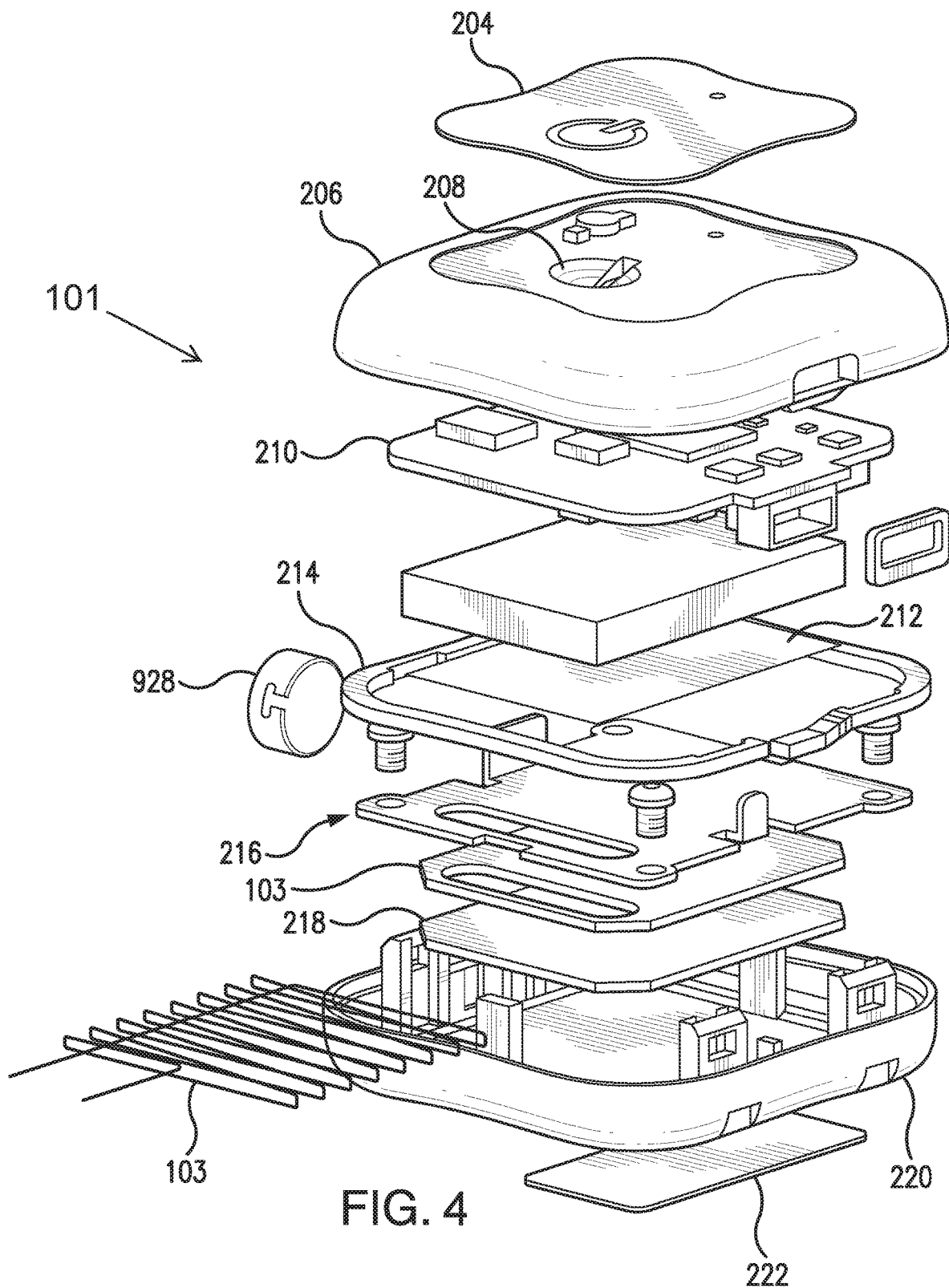
FIG. 4 is an exploded, perspective view of a transceiver embodying aspects of the invention.

FIGS. 3 and 4 are cross-sectional and exploded views, respectively, of a non-limiting embodiment of the transceiver 101, which may be included in the analyte monitoring system illustrated in FIG. 1. As illustrated in FIG. 4, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 3 and 4, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 5:
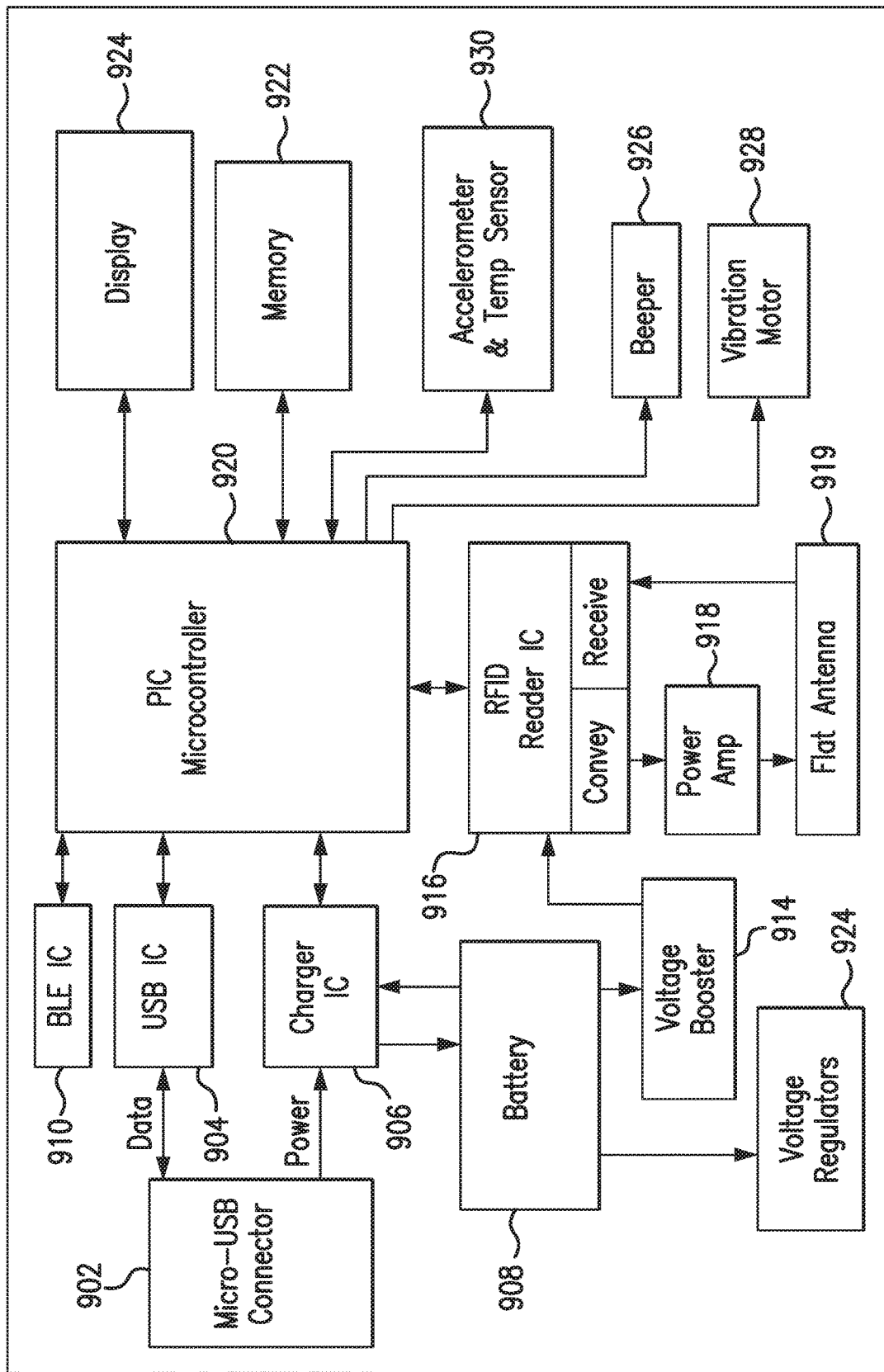
FIG. 5 is a schematic view illustrating a transceiver embodying aspects of the present invention.

FIG. 5 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

The transceiver 101 may include a peripheral interface controller (PIC) microcontroller 920 and a memory 922 (e.g., Flash memory), which may be non-volatile and/or capable of being electronically erased and/or rewritten. The PIC microcontroller 920 may control the overall operation of the transceiver 101. For example, the PIC microcontroller 920 may control the connector IC 904 or wireless communication IC 910 to transmit data via wired or wireless communication and/or control the RFID reader IC 916 to convey data via the inductive element 103. The PIC microcontroller 920 may also control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which PIC microcontroller 920 may control to display data (e.g., analyte levels values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, which may be used in the processing performed by the PIC microcontroller 920.

In some embodiments, the transceiver 101 may be a body-worn transceiver that is a rechargeable, external device worn over the sensor implantation or insertion site. The transceiver 101 may supply power to the proximate sensor 100, calculate analyte levels from data received from the sensor 100, and/or transmit the calculated analyte levels to a display device 105 (see FIG. 1). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2, 5, or 10 minutes) read sensor data and calculate an analyte level and an analyte level trend. From this information, the transceiver 101 may also determine if an alert and/or alarm condition exists, which may be signaled to the user (e.g., through vibration by vibration motor 928 and/or an LED of the transceiver's display 924 and/or a display of a display device 105).

The information from the transceiver 101 (e.g., calculated analyte levels, calculated analyte level trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting embodiments, the MMA may provide alarms, alerts, and/or notifications in addition to any alerts, alarms, and/or notifications received from the transceiver 101. In one embodiment, the MMA may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 of the analyte monitoring system 50 may receive raw signals indicative of an amount or concentration of an analyte in the interstitial fluid ("ISF") in proximity to the analyte indicator element 106 of the analyte sensor 100. In some embodiments, the transceiver 101 may receive the raw signals from the sensor 100 periodically (e.g., every 1, 2, 5, 10, 15, or 20 minutes). In some embodiments, the raw signals may include one or more measurements (e.g., one or more measurements indicative of the level of emission light 331 from the indicator molecules 104 as measured by the photodetector 224, one or more measurements indicative of the level of reference light 333 as measured by photodetector 226, and/or one or more temperature measurements as measured by the temperature transducer 670). In some embodiments, the transceiver 101 may use the received raw signals to calculate an ISF analyte level.

In some embodiments, the transceiver 101 may use the calculated ISF analyte level and one or more previously calculated ISF analyte levels to calculate a rate of change of the interstitial fluid analyte level ("ISF_ROC"). In some non-limiting embodiments, to calculate ISF_ROC, the transceiver 101 may use just the calculated ISF analyte level and the most recent previously calculated ISF analyte level and determine ISF_ROC as the difference between the calculated ISF analyte level and most recent previously calculated ISF analyte level divided by the time difference between a time stamp for the calculated ISF analyte level and a time stamp for the most recent previously calculated ISF analyte level. In some alternative embodiments, to calculate ISF_ROC, the transceiver 101 may use the calculated ISF analyte level and a plurality of the most recent previously calculated ISF analyte levels. In some non-limiting embodiments, the plurality of the most recent previously calculated ISF analyte levels may be, for example and without limitation, the previous two calculated ISF analyte levels, the previous 20 calculated ISF analyte levels, or any number of previously calculated ISF analyte levels in between (e.g., the previous 5 calculated analyte levels). In other alternative embodiments, to calculate ISF_ROC, the transceiver 101 may use the calculated ISF analyte level and the previously calculated ISF analyte levels that were calculated during a time period. In some non-limiting embodiments, the time period may be, for example and without limitation, the last one minute, the last 60 minutes, or any amount of time in between (e.g., the last 25 minutes). In some embodiments where the transceiver 101 uses the calculated ISF analyte level and more than one previously calculated ISF analyte levels to calculate ISF_ROC, the transceiver 101 may use, for example, linear or non-linear regression to calculate ISF_ROC.

In some embodiments, the transceiver 101 may convert the calculated ISF analyte level into a blood analyte level by performing a lag compensation, which compensates for the lag between blood analyte level and an ISF analyte level. In some embodiments, the transceiver 101 may calculate the blood analyte level using at least the calculated ISF analyte level and the calculated ISF_ROC. In some non-limiting embodiments, the transceiver 101 may calculate the blood analyte level as $ISF\_ROC/p_2+(1+p_3/p_2)*ISF\_analyte$, where $p_2$ is an analyte diffusion rate, $p_3$ is an analyte consumption rate, and ISF_analyte is the calculated ISF analyte level.

In some embodiments, the transceiver 101 may store one or more of the calculated ISF analyte level, calculated ISF_ROC, and calculated blood analyte level (e.g., in memory 922). In some embodiments, the transceiver 101 may convey the calculated blood analyte level to the display device 105, and the display device 105 may display the calculated blood analyte level.

In some embodiments, the transceiver 100 may store one or more of the calculated ISF analyte level, calculated ISF_ROC, and calculated blood analyte level (e.g., in memory 922). In some embodiments, the transceiver 100 may convey the calculated blood analyte level to the display device 105, and the display device 105 may display the calculated blood analyte level.

Figure 6:
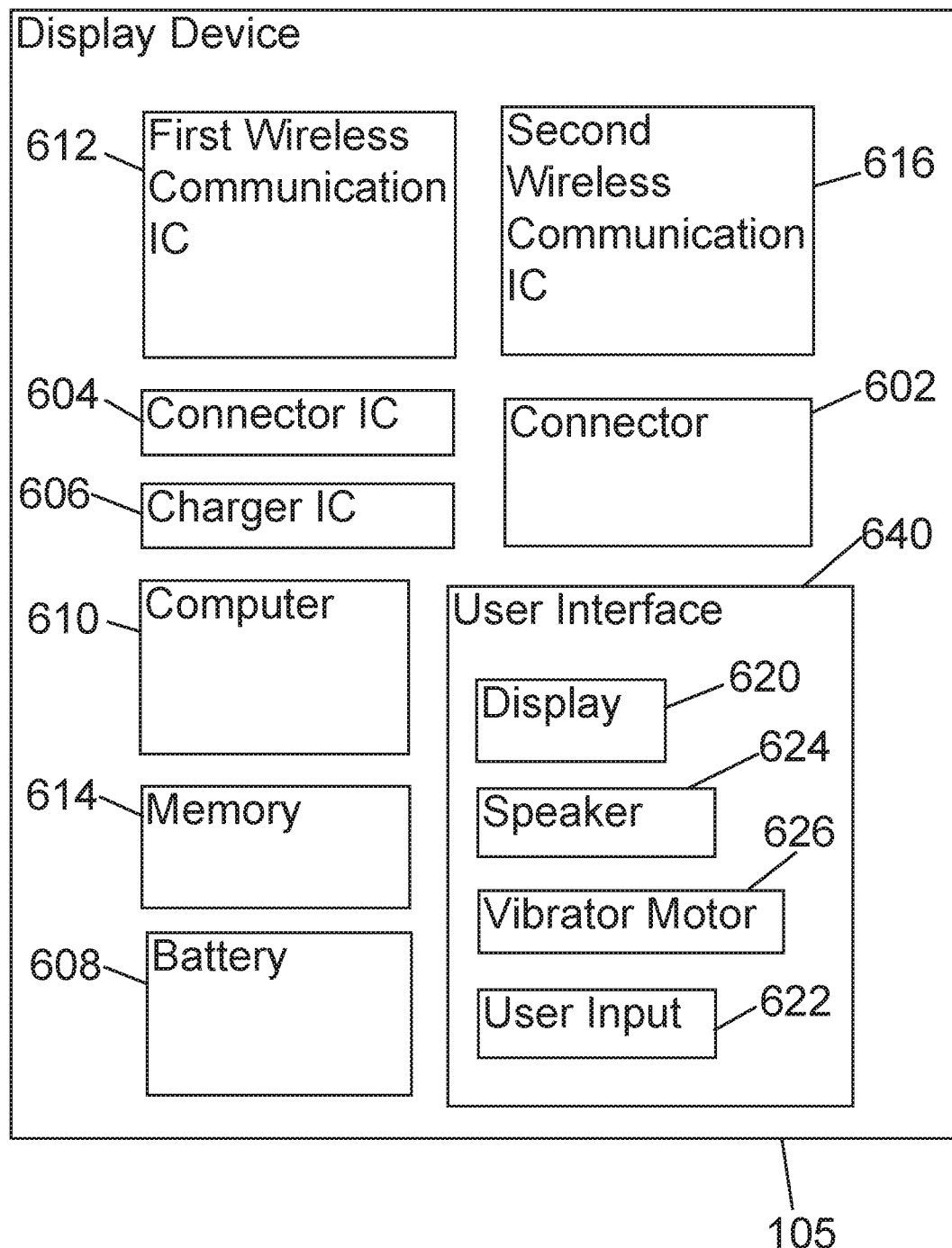
FIG. 6 illustrates a block diagram of a display device of the analyte monitoring system according to some embodiments.

FIG. 6 is a block diagram of a non-limiting embodiment of the display device 105 of the analyte monitoring system 50. As shown in FIG. 6, in some embodiments, the display device 105 may include one or more of a connector 602, a connector integrated circuit (IC) 604, a charger IC 606, a battery 608, a computer 610, a first wireless communication IC 612, a memory 614, a second wireless communication IC 616, and a user interface 640.

In some embodiments in which the display device 105 includes the connector 602, the connector 602 may be, for example and without limitation, a Micro-Universal Serial Bus (USB) connector. The connector 602 may enable a wired connection to an external device, such as a personal computer or transceiver 101 (e.g., via the connector 902 of the transceiver 101). The display device 105 may exchange data to and from the external device through the connector 602 and/or may receive power through the connector 602. In some embodiments, the connector IC 604 may be, for example and without limitation, a USB-IC, which may control transmission and receipt of data through the connector 602.

In some embodiments in which the display device 105 includes the charger IC 606, the charger IC 606 may receive power via the connector 602 and charge the battery 608. In some non-limiting embodiments, the battery 608 may be, for example and without limitation, a lithium-polymer battery. In some embodiments, the battery 608 may be rechargeable, may have a short recharge duration, and/or may have a small size.

In some embodiments, the display device 105 may include one or more connectors and/or one or more connector ICs in addition to (or as an alternative to) connector 602 and connector IC 604. For example, in some alternative embodiments, the display device 105 may include a spring-based connector (e.g., Pogo pin connector) in addition to (or as an alternative to) connector 602, and the display device 105 may use a connection established via the spring-based connector for wired communication to a personal computer or the transceiver 101 and/or to receive power, which may be used, for example, to charge the battery 608.

In some embodiments in which the display device 105 includes the first wireless communication IC 612, the first wireless communication IC 612 may enable wireless communication with one or more external devices, such as, for example, one or more personal computers, one or more transceivers 101, one or more other display devices 105, and/or one or more devices 109 (e.g., one or more wearable devices). In some non-limiting embodiments, the first wireless communication IC 612 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the first wireless communication IC 612 may be configured to wirelessly transmit data at a frequency greater than 1 gigahertz (e.g., 2.4 or 5 GHz). In some embodiments, the first wireless communication IC 612 may include an antenna (e.g., a Bluetooth antenna). In some non-limiting embodiments, the antenna of the first wireless communication IC 612 may be entirely contained within a housing of the display device 105. However, this is not required, and, in alternative embodiments, all or a portion of the antenna of the first wireless communication IC 612 may be external to the display device housing.

In some embodiments, the display device 105 may include a transceiver interface, which may enable communication by the display device 105 with one or more transceivers 101. In some embodiments, the transceiver interface may include the antenna of the first wireless communication IC 612 and/or the connector 602. In some non-limiting embodiments, the transceiver interface may additionally or alternatively include the first wireless communication IC 612 and/or the connector IC 604.

In some embodiments in which the display device 105 includes the second wireless communication IC 616, the second wireless communication IC 616 may enable the display device 105 to communicate with a remote data management system (DMS) and/or one or more remote devices (e.g., smartphones, servers, and/or personal computers) via wireless local area networks (e.g., Wi-Fi), cellular networks, and/or the Internet. In some non-limiting embodiments, the second wireless communication IC 616 may employ one or more wireless communication standards to wirelessly transmit data. In some embodiments, the second wireless communication IC 616 may include one or more antennas (e.g., a Wi-Fi antenna and/or one or more cellular antennas). In some non-limiting embodiments, the one or more antennas of the second wireless communication IC 616 may be entirely contained within a housing of the display device 105. However, this is not required, and, in alternative embodiments, all or a portion of the one or more antennas of the second wireless communication IC 616 may be external to the display device housing.

In some embodiments in which the display device 105 includes the memory 614, the memory 614 may be non-volatile and/or capable of being electronically erased and/or rewritten. In some embodiments, the memory 614 may be, for example and without limitations a Flash memory.

In some embodiments in which the display device 105 includes the computer 610, the computer 610 may control the overall operation of the display device 105. For example, the computer 610 may control the connector IC 604, the first wireless communication IC 612, and/or the second wireless communication IC 616 to transmit data via wired or wireless communication. The computer 610 may additionally or alternatively control processing of received data (e.g., analyte monitoring data received from the transceiver 101).

In some embodiments in which the display device 105 includes the user interface 640, the user interface 640 may include one or more of a display 620 and a user input 622. In some embodiments, the display 620 may be a liquid crystal display (LCD) and/or light emitting diode (LED) display. In some non-limiting embodiments, the user input 622 may include one or more buttons, a keyboard, a keypad, and/or a touchscreen. In some embodiments, the computer 610 may control the display 620 to display data (e.g., analyte levels, analyte level rate of change information, alerts, alarms, and/or notifications). In some embodiments, the user interface 640 may include one or more of a speaker 624 (e.g., a beeper) and a vibration motor 626, which may be activated, for example, in the event that a condition (e.g., a hypoglycemic or hyperglycemic condition) is met.

In some embodiments, the computer 610 may execute a mobile medical application (MMA). In some embodiments, the display device 105 may receive analyte monitoring data from the transceiver 101. In some non-limiting embodiments, the received analyte monitoring data may include one or more analyte levels, one or more analyte level rates of change, and/or one or more sensor measurements. In some embodiments, the received analyte monitoring data may additionally or alternatively include alarms, alerts, and/or notifications. In some embodiments, the MMA may display some or all of the received analyte monitoring data on the display 620 of the display device 105. In some alternative embodiments, the received analyte monitoring data may include one or more sensor measurements and does not include analyte levels, and the display device 105 may calculate one or more analyte levels using the one or more sensors measurements. In some alternative embodiments, the received analyte monitoring data may include one or more analyte levels but does not include analyte level rates of change, and the display device 105 may calculate one or more analyte level rates of change using the one or more analyte levels. In some non-limiting alternative embodiments, the display device 105 may calculate one or more analyte levels and calculate one or more analyte level rates of change using at least the one or more analyte levels calculated by the display device 105.

In some embodiments, the analyte monitoring system 50 may calibrate the conversion of raw signals to blood analyte levels. In some embodiments, the calibration may be performed approximately periodically (e.g., approximately every 12 or 24 hours). In some embodiments, the calibration may be performed using one or more reference measurements (e.g., one or more self-monitoring blood glucose (SMBG) measurements). In some non-limiting embodiments, the display device 105 may prompt a user for one or more reference measurements using, for example and without limitation the user interface 640 (e.g., the display 620, speaker 624, and/or vibration motor 626 of the user interface 640) of the display device 105. In some embodiments, the one or more reference measurements may be entered into the analyte monitoring system 50 using the user interface 640 (e.g., the user input 622 of the user interface 640) of the display device 105. In some embodiments, the display device 105 may convey one or more references measurements to the transceiver 101 (e.g., using the first wireless communication IC 612 and/or the connector 602). In some embodiments, the transceiver 101 may receive the one or more reference measurements from the display device 105 and use the one or more reference measurements to perform the calibration. In response, the user may enter the one or more reference measurements into the display device 105 using, for example and without limitation, the user interface 640 (e.g., the user input 622 of the user interface 640) of the display device 105.

Figure 7:
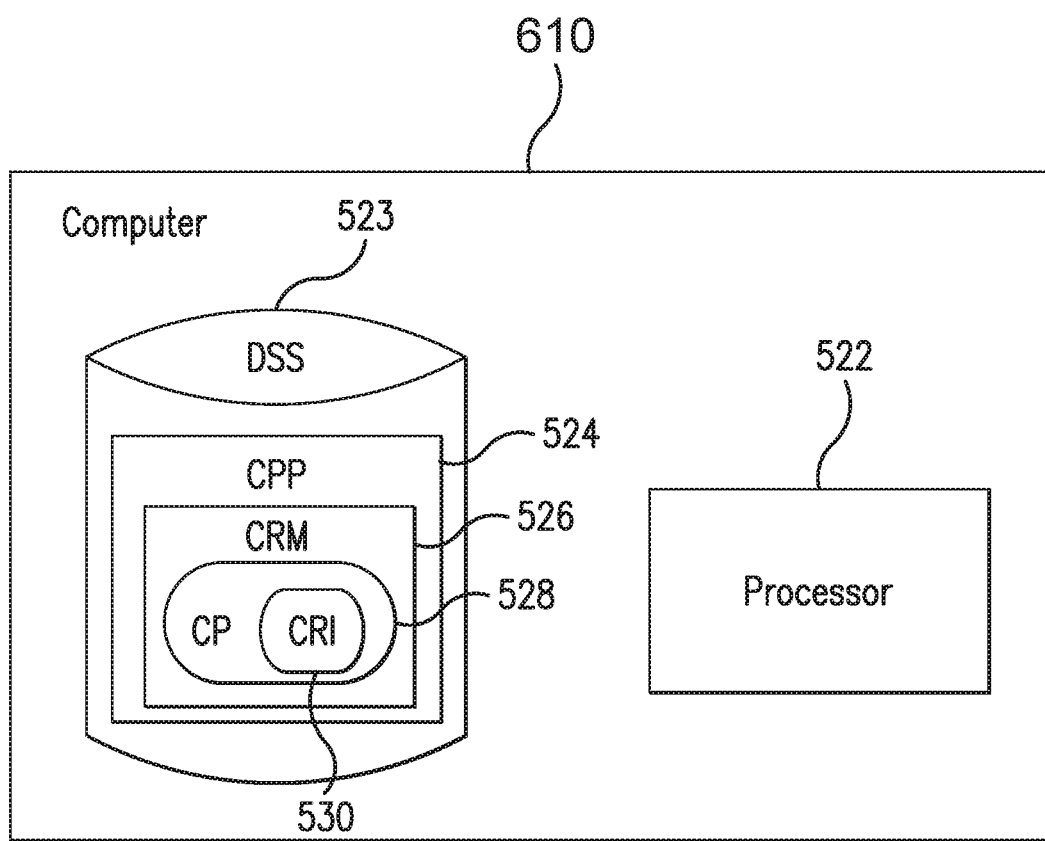
FIG. 7 illustrates a block diagram of a computer of the display device of the analyte monitoring system according to some embodiments.

FIG. 7 is a block diagram of a non-limiting embodiment of the computer 610 of the analyte monitoring system 50. As shown in FIG. 7, in some embodiments, the computer 610 may include one or more processors 522 (e.g., a general purpose microprocessor) and/or one or more circuits, such as an application specific integrated circuit (ASIC), field-programmable gate arrays (FPGAs), a logic circuit, and the like. In some embodiments, the computer 610 may include a data storage system (DSS) 523. The DSS 523 may include one or more non-volatile storage devices and/or one or more volatile storage devices (e.g., random access memory (RAM)). In embodiments where the computer 610 includes a processor 522, the DSS 523 may include a computer program product (CPP) 524. CPP 524 may include or be a computer readable medium (CRM) 526. The CRM 526 may store a computer program (CP) 528 comprising computer readable instructions (CRI) 530. In some embodiments, the CRM 526 may store, among other programs, the MMA, and the CRI 530 may include one or more instructions of the MMA. The CRM 526 may be a non-transitory computer readable medium, such as, but not limited to, magnetic media (e.g., a hard disk), optical media (e.g., a DVD), solid state devices (e.g., random access memory (RAM) or flash memory), and the like. In some embodiments, the CRI 530 of computer program 528 may be configured such that when executed by processor 522, the CRI 530 causes the computer 610 to perform steps described below (e.g., steps described below with reference to the MMA). In other embodiments, the computer 610 may be configured to perform steps described herein without the need for a computer program. That is, for example, the computer 610 may consist merely of one or more ASICs. Hence, the features of the embodiments described herein may be implemented in hardware and/or software.

In some embodiments in which the user interface 640 of the display device 105 includes the display 618, the MMA may cause the display device 105 to provide a series of graphical control elements or widgets in the user interface 640, such as a graphical user interface (GUI), shown on the display 618. The MMA may, for example without limitation, cause the display device 105 to display analyte related information in a GUI such as, but not limited to: one or more of analyte information, current analyte levels, past analyte levels, predicted analyte levels, user notifications, analyte status alerts and alarms, trend graphs, analyte level rate of change or trend arrows, and user-entered events. In some embodiments, the MMA may provide one or more graphical control elements that may allow a user to manipulate aspects of the one or more display screens. Although aspects of the MMA are illustrated and described in the context of glucose monitoring system embodiments, this is not required, and, in some alternative embodiments, the MMA may be employed in other types of analyte monitoring systems.

In some embodiments where the display device 105 communicates with a transceiver 101, which in turn obtains sensor measurement data from the analyte sensor 100, the MMA may cause the display device 105 to receive and display one or more of analyte data, trends, graphs, alarms, and alerts from the transceiver 101. In some embodiments, the MMA may store analyte level history and statistics for a patient on the display device 105 (e.g., in memory 614 and/or DSS 533) and/or in a remote data storage system.

In some embodiments, a user of the display device 105, which may be the same or different individual as patient, may initiate the download of the MMA from a central repository over a wireless cellular network or packet-switched network, such as the Internet. Different versions of the MMA may be provided to work with different commercial operating systems, such as the Android OS or Apple OS running on commercial smart phones, tablets, and the like. For example, where display device 105 is an Apple iPhone, the user may cause the display device 105 to access the Apple iTunes store to download a MMA compatible with an Apple OS, whereas where the display device 105 is an Android mobile device, the user may cause the display device 105 to access the Android App Store to download a MMA compatible with an Android OS.

Figure 8:
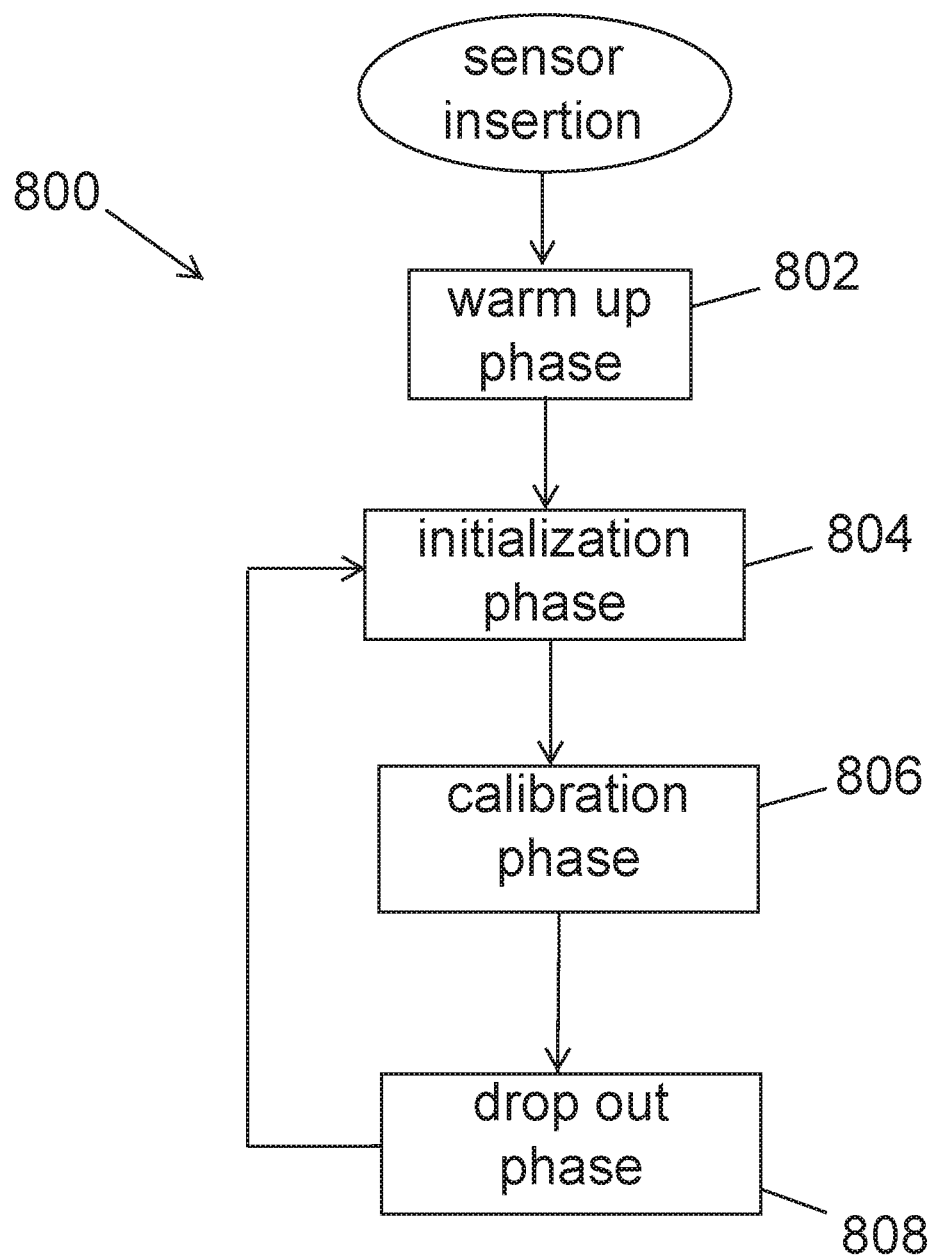
FIG. 8 is a flow chart illustrating a process for controlling initialization and calibration of an analyte monitoring system embodying aspects of the present invention.

FIG. 8 is a flow chart illustrating a process 800 for controlling initialization and calibration of an analyte monitoring system 50. In some embodiments, the transceiver 101 performs one or more steps of the control process 800. In some non-limiting embodiments, the PIC microcontroller 920 of the transceiver 101 performs one or more steps of the control process 800. In some embodiments, the process 800 may begin after insertion or implantation of the analyte sensor 100.

In some embodiments, the process 800 may begin with a warm up phase 802 in which the transceiver 101 allows the sensor 100 to adjust to being fully or partially in the body. In some non-limiting embodiments, the warm up phase 802 may give the analyte indicator element 106 time to hydrate. In some non-limiting embodiments, the transceiver 101 stays in the warm up phase 802 for a predetermined period of time such as, for example and without limitation, 12 or 24 hours. However, this is not required, and, in some alternative embodiments, the transceiver 101 may monitor sensor conditions during the warm up phase 802 and exit the warm up phase 802 after the sensor conditions have stabilized. In some embodiments, after completion of the warm up phase 802, the process 800 may proceed to an initialization phase 804. In some alternative embodiments, the warm up phase 802 may not be necessary (e.g., when the analyte sensor 100 is an external sensor or does not need time to acclimate to being inside the body). In these alternative embodiments, the process 800 may begin in an initialization step 804.

In some embodiments, in the initialization phase 804, the transceiver 101 may receive sensor data. In some non-limiting embodiments, the transceiver 101 may receive the sensor data periodically (e.g., every 1, 2, 5, 10, 15, or 20 minutes). In some embodiments, in the initialization phase 804, the transceiver 101 may receive one or more reference measurements. In some non-limiting embodiments, the transceiver 101 may receive three or more reference measurements in the initialization phase 804. In some non-limiting embodiments, the transceiver 101 may receive the reference measurements periodically (e.g., approximately every 6 hours). In some embodiments, the transceiver 101 may store the reference measurements in a calibration point memory, which may be, for example and without limitation, a circular buffer. In some embodiments, the transceiver 101 may use the one or more reference measurements as calibration points to perform an initial calibration of the conversion function used to calculate blood analyte measurements from the sensor data. In some embodiments, the transceiver 101 may receive the one or more reference measurements from the user interface of the display device 105. In some non-limiting embodiments, the transceiver 101 may cause the display device 105 to prompt a user for the one or more reference measurements using, for example and without limitation the user interface 640 (e.g., the display 620, speaker 624, and/or vibration motor 626 of the user interface 640) of the display device 105. In response, the user may enter the one or more reference measurements into the display device 105 using, for example and without limitation, the user interface 640 (e.g., the user input 622 of the user interface 640) of the display device 105.

In some non-limiting embodiments, during the initialization phase 804, no analyte measurements are displayed to the user. In some embodiments, after the completion of the initialization phase 804, the process 800 may proceed to a calibration phase 806. In some embodiments, the calibration phase 806 may be a steady state phase.

In some embodiments, in the calibration phase 806, the transceiver 101 may receive sensor data and calculate blood analyte measurements using the conversion function and the received sensor data. In some non-limiting embodiments, the transceiver 101 may receive the sensor data periodically (e.g., every 1, 2, 5, 10, 15, or 20 minutes). In some embodiments, the transceiver 101 may display one or more blood analyte measurements. In some non-limiting embodiments, in the calibration phase 806, the transceiver 101 may display the one or more blood analyte measurements by transmitting them to the display device 105 for display.

In some embodiments, in the calibration phase 806, the transceiver 101 may receive one or more reference measurements. In some non-limiting embodiments, the transceiver 101 may receive the reference measurements periodically (e.g., approximately every 12 hours). In some non-limiting embodiments, the transceiver 101 may receive the reference measurements less frequently than in the initialization phase 804. However, this is not required. It is also not required that the transceiver 101 receive reference measurements periodically, and, in some alternative embodiments, the transceiver 101 may receive reference measurements on an as-needed basis (e.g., as determined by the transceiver 101 by analyzing the sensor data). In some embodiments, the transceiver 101 may receive the reference measurements from the display device 105. In some non-limiting embodiments, in the calibration phase 806, the transceiver 101 may cause the display device 105 to prompt a user for the one or more reference measurements using, for example and without limitation the user interface 640 of the display device 105. In response, the user may enter the one or more reference measurements into the display device 105 using, for example and without limitation, the user interface 640 of the display device 105.

In some embodiments, in the sensor dropout phase 808, the transceiver 101 may receive sensor data from the sensor 100, but no analyte measurements are displayed to the user. In some embodiments, the process 800 may remain in the dropout phase 808 for a period of time (e.g., at least six hours) before proceeding back to the initialization phase 804. However, the sensor dropout phase 808 is not necessary, and, in some alternative embodiments, the process 800 may proceed directly to the initialization phase 804 from the calibration phase 806.

Figure 9:
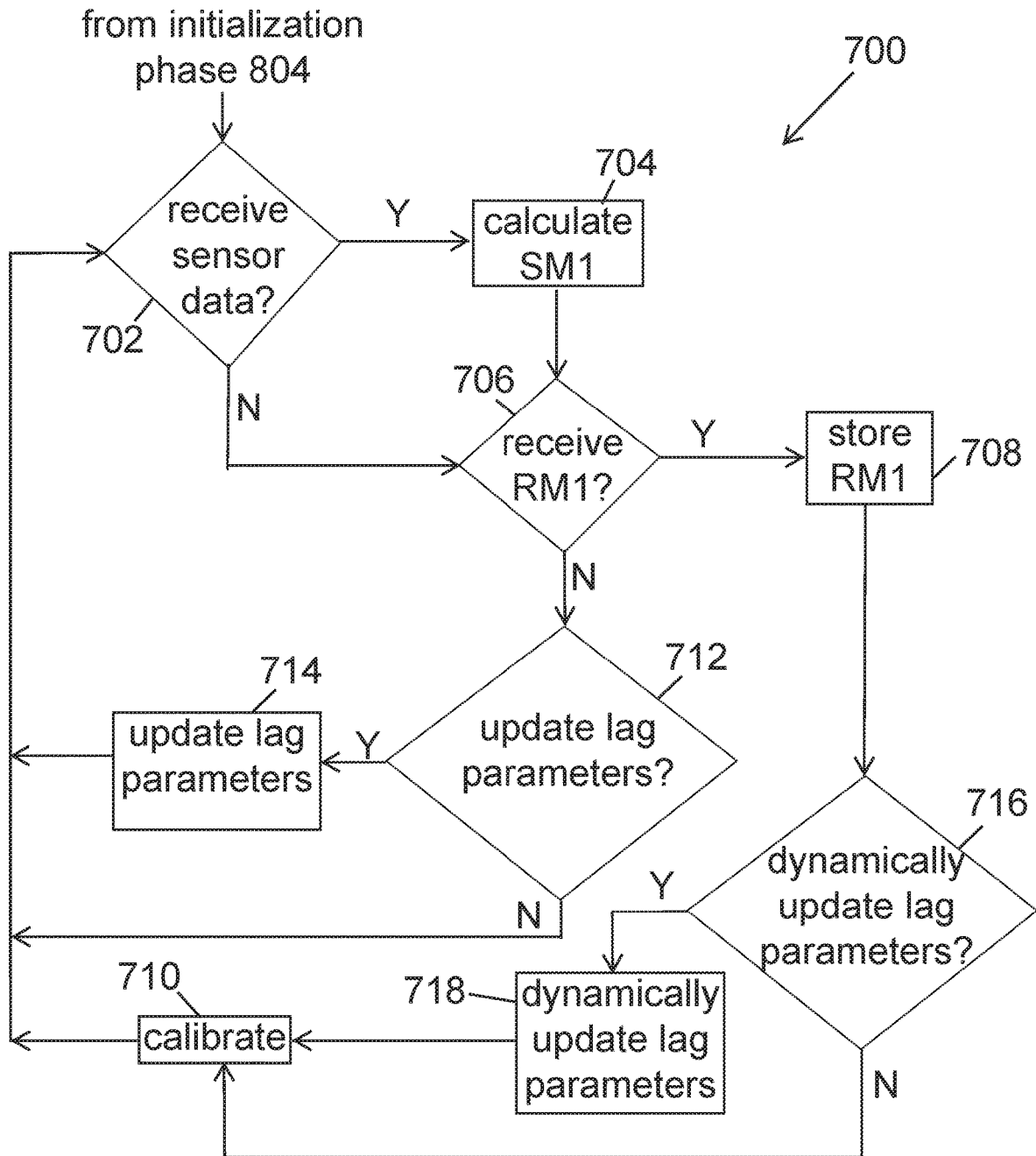
FIG. 9 is a flow chart illustrating a calibration process embodying aspects of the present invention.

FIG. 9 is a flow chart illustrating a calibration process 700, which may be performed during the calibration phase 806 of the control process 800 illustrated in FIG. 8. In some embodiments, the transceiver 101 may perform one or more steps of the calibration process 700. In some non-limiting embodiments, the PIC microcontroller 920 of the transceiver 101 may perform one or more steps of the calibration process 700.

In some embodiments, as shown in FIG. 9, the calibration process 700 may include a step 702 in which the transceiver 101 determines whether the transceiver 101 has received sensor data (e.g., light and/or temperature measurements) from the sensor 100. In some embodiments, the sensor data may be received following a command (e.g., a measurement command or a read sensor data command) conveyed from the transceiver 101 to the sensor 100. However, this is not required, and, in some alternative embodiments, the sensor 100 may control when sensor data is conveyed to the transceiver 101, or the sensor 100 may continuously convey sensor data to the transceiver 101. In some non-limiting embodiments, the transceiver 101 may receive the sensor data periodically (e.g., every 1, 2, 5, 10, 15, or 20 minutes). In some embodiments, the transceiver 101 may receive the sensor data wirelessly. For example and without limitation, in some non-limiting embodiments, the transceiver 101 may receive the sensor data by detecting modulations in an electromagnetic wave generated by the sensor 100 (e.g., by detecting modulations in the current flowing through the coil 103 of the transceiver 101). However, this is not required, and, in some alternative embodiments, the transceiver 101 may receive the sensor data via a wired connection to the sensor 100. In some non-limiting embodiments, if the sensor has received sensor data, the calibration process 700 may proceed from step 702 to a measurement calculation step 704. In some non-limiting embodiments, if the transceiver 101 has not received sensor data, the calibration process 700 may proceed from step 702 to a step 706.

In some non-limiting embodiments, the calibration process 700 may include the measurement calculation step 704. In some embodiments, the step 704 may include calculating a sensor measurement SM1 using the current conversion function and the received sensor data. In some embodiments, the sensor measurement SM1 may be a measurement of a blood analyte level. In some embodiments, the measurement calculation step 704 may include calculating an ISF analyte level, an ISF_ROC, and the blood analyte level.

In some non-limiting embodiments, in the measurement calculation step 704, the transceiver 101 may calculate the ISF analyte level using the received sensor data. In some embodiments, the ISF analyte level may be a measurement of the amount or concentration of the analyte in the interstitial fluid in proximity to the analyte indicator element 106. In some non-limiting embodiments, calculation of the ISF analyte level may include, for example and without limitation, some or all of the features described in U.S. application Ser. No. 13/937,871, filed on Jul. 9, 2013, which is incorporated by reference herein in its entirety.

In some non-limiting embodiments, in the measurement calculation step 704, the transceiver 101 may calculate the ISF_ROC using at least the calculated ISF analyte level. In some non-limiting embodiments, the transceiver 101 may calculate the ISF_ROC using at least the calculated ISF analyte level and one or more previously calculated ISF analyte levels (e.g., one or more ISF analyte levels calculated using previously received sensor data).

In some non-limiting embodiments, in the measurement calculation step 704, the transceiver 101 may calculate the blood analyte level by performing a lag compensation. In some embodiments, the transceiver 101 may calculate the blood analyte level using at least the calculated ISF analyte level and the calculated ISF_ROC. In some non-limiting embodiments, the transceiver 101 may calculate the blood analyte level using the formula ISF_ROC/$p_2$+(1+$p_3$/$p_2$)*ISF_analyte, where $p_2$ is the analyte diffusion rate, $p_3$ is the analyte consumption rate, ISF_ROC is the calculated ISF_ROC, and ISF_analyte is the calculated ISF analyte level. However, this is not required, and some alternative embodiments may use a different formula for calculating the blood analyte level.

For example, in some non-limiting alternative embodiments, the transceiver 101 may calculate the sensor measurement SM1 by utilizing a two-compartment model, such as, for example:

$$\frac{dC_2}{dt} = p_2 * [C_1(t) - C_2(t)] - p_3 * C_2(t)$$

In some embodiments, $C_2$ may represent the ISF analyte level. In some embodiments, $C_1$ may represent the sensor measurement SM1, which may be a blood analyte level. In some embodiments, $p_2$ and $p_3$ may represent an analyte diffusion rate and an analyte consumption rate, respectively, as the analyte diffuses from the ISF to the blood.

In some embodiments, the transceiver 101 may solve for the concentration of analyte in blood ($C_1$) according to the following two-compartment model, wherein the variables retain the same definition as described above:

$$C_1(t) = \frac{1}{p_2}\frac{dC_2}{dt} + \left(1 + \frac{p_3}{p_2}\right) * C_2(t)$$

In some non-limiting embodiments, the lag parameters may be one or more of 1/$p_2$ and $p_3$/$p_2$. In some non-limiting parameters, the lag parameters may be one or more of $p_2$ and $p_3$.

In some non-limiting embodiments, the transceiver 101 may employ an asymmetrical lag methodology when converting an ISF analyte level into a blood analyte level. In some embodiments, the asymmetrical lag methodology may reflect physiological analyte level changes more accurately than a symmetrical lag methodology. In some non-limiting embodiments, the asymmetrical lag methodology may more reflect physiological glucose level changes during a hypoglycemic state more accurately than a symmetrical lag methodology. In some non-limiting embodiments, the asymmetrical lag methodology may be designed to more closely mimic the normal physiological response to (and protection against) the hypoglycemic state. In some non-limiting embodiments, the asymmetrical lag methodology may include one or more of: (i) decelerating the rate of change in further falling glucose levels in hypoglycemia and (ii) accelerating glucose rises when recovering from a hypoglycemic or low blood glucose event.

In some non-limiting embodiments in which the asymmetrical lag methodology decelerates the falling rate of change, the asymmetrical lag methodology may include determining whether the calculated ISF analyte level is less than or equal to a low ISF analyte level threshold (e.g., a hypoglycemia ISF threshold). In some non-limiting embodiments, the low ISF analyte level threshold may be, for example and without limitation, 70 mg/dL, but other values may be used in alternative embodiments. In some non-limiting embodiments, the asymmetrical lag methodology may include determining whether the calculated ISF_ROC is less than a low analyte level ISF_ROC lower limit threshold (e.g., a hypoglycemia ISF_ROC lower limit threshold). In some non-limiting embodiments, the low analyte level ISF_ROC lower limit threshold may be, for example and without limitation, −1.3 mg/dL/min, but other values may be used in alternative embodiments. In some non-limiting embodiments, if the calculated ISF analyte level is less than or equal to the low ISF analyte level threshold and the calculated ISF_ROC is less than a low analyte level ISF_ROC lower limit threshold, the asymmetrical lag methodology may include using the low analyte level ISF_ROC lower limit threshold instead of the calculated ISF_ROC to calculate the blood analyte level.

In some non-limiting embodiments in which the asymmetrical lag methodology decelerates the falling rate of change, the asymmetrical lag methodology may additionally or alternatively include determining whether the calculated blood analyte level is less than a low analyte level linear fit threshold (e.g., a hypoglycemia linear fit threshold). In some non-limiting embodiments, the low analyte level linear fit threshold may be lower than the low ISF analyte level threshold. In some non-limiting embodiments, the low analyte level linear fit threshold may be, for example and without limitation, 50 mg/dL, but other values may be used in alternative embodiments. In some non-limiting embodiments, if the calculated blood analyte level is less than the low analyte level linear fit threshold, the asymmetrical lag methodology may adjust the calculated blood analyte level using the following linear equation: adjusted BG=BG*LinearFit_slope+LinearFit_intercept, wherein the adjusted BG is the adjusted blood analyte level, and BG is the calculated blood analyte level. In some non-limiting embodiments, the LinearFit_slope and LinearFit_intercept may be determined using experimental data.

In some non-limiting embodiments, the asymmetrical lag methodology may include determining whether the calculated blood analyte level (or the adjusted blood analyte level if the calculated blood analyte level has been adjusted using the linear equation) is less than a low blood analyte level threshold (e.g., a hypoglycemia blood threshold). In some non-limiting embodiments, the low blood analyte level threshold may be, for example and without limitation, 70 mg/dL, but other values may be used in alternative embodiments. In some non-limiting embodiments, the asymmetrical lag methodology may include calculating an instantaneous blood analyte level rate of change (e.g., using the current blood analyte and one or more previous blood analyte levels). In some non-limiting embodiments, the asymmetrical lag methodology may include determining whether the calculated instantaneous blood analyte level rate of change is less than a low blood analyte level rate of change threshold (e.g., a hypoglycemia blood analyte level rate of change threshold). In some non-limiting embodiments, the low blood analyte level rate of change threshold may be, for example and without limitation, −1.2 mg/dL/min, but other values may be used in alternative embodiments. In some non-limiting embodiments, if the calculated blood analyte level is less than the low blood analyte level and the calculated instantaneous blood analyte level rate of change is less than the low blood analyte level rate of change threshold, the asymmetrical lag methodology may update the current blood analyte level as follows: BG(n)=BG(n−1)+Low_BG_ROC_Limit*dTime, where BG(n) is the current calculated blood analyte, BG(n−1) is the previous calculated blood analyte level, Low_BG_ROC_Limit is the low blood analyte level rate of change threshold, and dTime is the number of minutes between the current and the previous sensor measurements.

In some non-limiting embodiments in which the asymmetrical lag methodology accelerates glucose rises during recovery from a hypoglycemic or low blood glucose event, the asymmetrical lag methodology may include determining whether the calculated ISF analyte level is less than or equal to an adjust diffusion time threshold. In some non-limiting embodiments, the asymmetrical lag methodology may include determining whether the ISF analyte level is rising. In some non-limiting embodiments, if the calculated ISF analyte level is less than or equal to an adjust diffusion time threshold and rising, the asymmetrical lag methodology may include multiplying a lag parameter associated with diffusion time (e.g., $1/p_2$) by a factor [e.g., 1.1], and using the adjusted lag parameter in the conversion function to calculate the blood analyte level. In some non-limiting embodiments, the factor may be, for example and without limitation, 1.1, but other factors may be used in alternative embodiments.

In some embodiments, in step 704, the transceiver 101 may display the calculated sensor measurement SM1. In some non-limiting embodiments, the transceiver 101 may display the sensor measurement SM1 by transmitting it to the display device 105 for display.

In some non-limiting embodiments, the calibration process 700 may include the step 706 in which the transceiver 101 determines whether the transceiver 101 has received a reference measurement RM1. The reference measurement RM1 may be, for example and without limitation, an SMBG measurement obtained from, for example and without limitation, a finger-stick blood sample. In some embodiments, the transceiver 101 may receive reference measurements periodically or on an as-needed basis. In some embodiments, the transceiver 101 may receive the reference measurement RM1 from the display device 105. In some non-limiting embodiments, the transceiver 101 may cause the display device 105 to prompt a user for the reference measurement RM1, and, in response, the user may enter the reference measurement RM1 into the display device 105. In some alternative embodiments, the transceiver 101 may prompt a user for the reference measurement RM1, and, in response, the user may enter the reference measurement RM1 directly into the transceiver 101.

In some embodiments, the transceiver 101 may receive the reference measurement RM1 with a reference time stamp. In some embodiments, the device into which the reference measurement RM1 is entered by a user (e.g., the display device 105 or the transceiver 101) may assign the reference time stamp to the reference measurement RM1 when the user enters the reference measurement RM1 into the device, and the reference time stamp may indicate the time at which the user entered the reference measurement RM1 into the device. However, this is not required, and, in some alternative embodiments, the reference time stamp may be a time entered by a user to indicate a time at which the reference measurement was taken (e.g., a time at which blood was drawn for an SMBG measurement). In some non-limiting alternative embodiments, a user may enter a time at which a reference measurement was taken before, at the same time as, or after the user enters a reference measurement RM1. In one non-limiting alternative embodiment, the device into which the user enters the reference measurement RM1 (e.g., the display device 105 or the transceiver 101) may prompt the user to enter a time at which the reference measurement was taken. In some non-limiting embodiments, the device that prompts the user for the reference measurement RM1 (e.g., the display device 105 or the transceiver 101) may additionally prompt the user to enter a time at which the reference measurement was taken. In some other alternative embodiments, transceiver 101 may assign the reference time stamp to the reference measurement RM1 when the transceiver 101 receives the reference measurement RM1 from the display device 105, and the reference time stamp may indicate the time at which the transceiver 101 receives the reference measurement RM1 from the display device 105.

In some embodiments, if the transceiver 101 has not received a reference measurement RM1, the calibration process 700 may proceed to a step 712. In some embodiments, if the transceiver 101 has received a reference measurement RM1, the calibration process 700 may proceed to a step 708.

In some non-limiting embodiments, the calibration process 700 may include the step 712 in which the transceiver 101 determines whether to update one or more lag parameters (e.g., one or more of $1/p_2$ and $p_3/p_2$ or one or more of the analyte diffusion rate $p_2$ and the analyte consumption rate $p_3$). In some embodiments, the decision of whether to update the parameters of the transport model will be made according to, for example and without limitation, whether a length of time has passed since the parameters were last updated. For example and without limitation, in one non-limiting embodiment, the transceiver 101 may update one or more of the lag parameters periodically (e.g., every 1, 2, 5, 10, 20, or 30 days). In some alterative embodiments, the life of the analyte sensor 100 after insertion may be divided into a number of time periods (e.g., 2, 3, 4, 5, 6, 7, 8, 10, 15, 20, 50, or 100 time periods), and the decision of whether to update the parameters of the transport model will be made according to whether the life of the analyte sensor 100 has passed into a new time period, and different lag parameters may be associated with the different time periods. For example and without limitation, in one non-limiting alternative embodiment, the life of the analyte sensor 100 after insertion may be divided into the following six periods: (1) Day 0 to Day 5, (2) Day 5 to Day 10, (3) Day 10 to Day 20, (4) Day 20 to Day 45, (5) Day 45 to Day 75, and (6) greater than Day 75, and different lag parameters may be associated with the six periods.

If the transceiver 101 determines that one or more of the lag parameters should be updated, the calibration process 700 may proceed to a lag parameter updating step 714 in which the transceiver 101 may update one or more of the lag parameters. In some embodiments, lag parameters associated with the different time periods may be stored in a memory of the transceiver 101 (e.g., memory 922). In some non-limiting embodiments, the memory may store different values for one or more of $1/p_2$ and $p_3/p_2$. For example and without limitation, in one non-limiting embodiment, the memory may store the following values for $1/p_2$: 1689 for the Day 0 to Day 5 period and for the Day 5 to Day 10 period, 1478 for the Day 10 to Day 20 period, and 1230 for the Day 20 to Day 45 period and for the greater than Day 75 period. For example and without limitation, in one non-limiting embodiment, the memory may store the following values for $p_3/p_2$: 0.1551 for the Day 0 to Day 5 period and for the Day 5 to Day 10 period, 0.0586 for the Day 10 to Day 20 period, and 0.1 for the Day 20 to Day 45 period and for the greater than Day 75 period. Although the stored values for $1/p_2$ and $p_3/p_2$ are the same for the Day 0 to Day 5 and Day 5 to Day 10 periods and for the Day 20 to Day 45 and greater than Day 75 periods in the non-limiting examples set forth above, this is not required, and, in some non-limiting alternative embodiments, the stored values for one or more of $1/p_2$ and $p_3/p_2$ may be different in each of the periods. In addition, some non-limiting alternative embodiments, instead of storing values for one or more of $1/p_2$ and $p_3/p_2$, the memory may store different values for one or more of $p_2$ and $p_3$.

In some non-limiting embodiments, the transceiver 101 may update one or more of the lag parameters to be lag parameters associated with a time period into which the life of the analyte sensor 100 has entered. In some embodiments, after updating the lag parameters, the calibration process 700 may proceed from step 714 back to step 702. In some embodiments, the transceiver 101 may then use a conversion function with the one or more updated lag parameters when calculating one or more subsequent sensor measurements SM1 (e.g., when the transceiver 101 performs step 704 after received additional sensor data in step 702).

In some embodiments, in step 712, if the transceiver 101 does not determine that one or more lag parameters should be updated, the calibration process 700 may proceed back to step 702, and the calibration process 700 may continue without updating any lag parameters and using the current conversion function to calculate sensor measurements when sensor data is received until a reference measurement RM1 is received (or the lag parameters are updated).

In some non-limiting embodiments, the calibration process 700 may include a step 708 in which the reference measurement RM1 is stored in, for example, a calibration point memory (e.g., a circular buffer). In some embodiments, the reference measurement RM1 may be stored in the calibration point memory with a corresponding reference time stamp. As explained above, in some embodiments, the reference time stamp may indicate the time at which a user entered the reference measurement RM1 (either into the display device 105 or the into the transceiver 101), the time at which the reference measurement was taken (e.g., the time at which blood was drawn for an SMBG measurement), or the time at which the transceiver 101 received the reference measurement from the display device 105. In some embodiments, the calibration process 700 may proceed directly from step 708 to a step 710 (and the process 700 may not include dynamic lag parameter update steps 716 and 718). In some non-limiting alternative embodiments, as illustrated in FIG. 9, the calibration process 700 may include dynamic lag parameter update steps 716 and 718, and the calibration process 700 may proceed from step 708 to the step 716.

In some embodiments, the calibration process 700 may include a step 716 in which the transceiver 101 determines whether to update dynamically one or more lag parameters (e.g., one or more of $1/p_2$ and $p_3/p_2$ or one or more of the analyte diffusion rate $p_2$ and the analyte consumption rate $p_3$). In some embodiments, the transceiver 101 may determine that no dynamic update is needed if only one reference measurement RM1 has been stored in the calibration point memory (i.e., if the reference measurement RM1 stored in step 708 was the first calibration point). In some embodiments, the transceiver 101 may additionally or alternatively determine that no dynamic update is needed if one or more of the lag parameters were updated recently (e.g., in step 714). In some non-limiting embodiments, one or more of the lag parameters may have been updated recently if the reference measurement RM1 most recently received and stored in the calibration point memory is the first calibration point received and stored since updating one or more of the lag parameters in step 714. For example and without limitation, in non-limiting some embodiments, one or more of the lag parameters may have been updated recently if the reference measurement RM1 most recently received and stored in the calibration point memory is the first reference measurement RM1 stored in the calibration point received and stored during the current time period (e.g., the current one of the following six time periods: (1) Day 0 to Day 5, (2) Day 5 to Day 10, (3) Day 10 to Day 20, (4) Day 20 to Day 45, (5) Day 45 to Day 75, and (6) greater than Day 75). In some embodiments, if the transceiver 101 determines in step 716 that no dynamic update is needed, the process 700 may proceed from step 716 to a calibration step 710. However, if the transceiver 101 determines in step 716 to update dynamically one or more lag parameters, the process 700 may proceed from step 716 to a dynamic lag parameter update step 718.

In some embodiments, the calibration process 700 may include a dynamic lag parameter update step 718 in which the transceiver 101 updates dynamically one or more of the lag parameters of the analyte transport model. In some embodiments, the lag parameters may be L1 and L2. In some embodiments, lag parameters L1 and L2 may be $1/p_2$ and $p_3/p_2$, respectively. In some alternative embodiments, L1 and L2 may be the analyte diffusion rate $p_2$ and the analyte consumption rate $p_3$, respectively.

In some embodiments, the transceiver 101 may characterize accuracy using one or more reference measurements stored in the calibration point memory. In some non-limiting embodiments, the transceiver 101 may characterize accuracy using the most recent reference measurements (e.g., the most-recent 10 reference measurements). In some non-limiting embodiments, the transceiver 101 may use the recent reference measurements in a weighted fashion. In some non-limiting embodiments, the transceiver 101 may update the lag parameters using the lag parameters that most accurately fit the most recent reference measurements.

In some non-limiting embodiments, the transceiver 101 may update one or more of the lag parameters L1 and L2 using a two parameter (Mop and NMop) method. In some non-limiting embodiments, the two parameter method may use a Minimal Deviation Divergence Method (MDDM) to determine the parameters with the best fit and minimal divergence from the previous parameters. In some non-limiting embodiments, in the two parameter method with MDDM, at calibration time $t_n$, let $Mop(t_n)=L1(t_n)$ and $NMop(t_n)=L2(t_n)$. In some embodiments, the two parameter method with MDDM may include obtaining N candidate Mop and NMop values based on their previous values and the search step specified in a sensor calibration file. In one non-limiting example, N may be equal to 20, the search steps may be 50 for Mop and 0.1 for NMop, the actual parameter incremental step may be calculated as (50+50)/20=5 for Mop and (0.1+0.1)/20=0.01 for NMop, and the resulting candidate Mop and NMop values may be:

$$NMop_{try(t_n,1)} = NMop(t_{n-1}) - 0.1$$

$$NMop_{try(t_n,2)} = NMop(t_{n-1}) - 0.1 + 0.01$$

$$NMop_{try(t_n,3)} = NMop(t_{n-1}) - 0.1 + 0.02$$

$$\vdots$$

$$NMop_{try(t_n,i)} = NMop(t_{n-1}) - 0.1 + 0.01*(i-1)$$

$$\vdots$$

$$NMop_{try(t_n,20)} = NMop(t_{n-1}) - 0.1 + 0.19$$

and $$Mop_{try(t_n,1)} = Mop(t_{n-1}) - 50$$

$$Mop_{try(t_n,2)} = Mop(t_{n-1}) - 50 + 5$$

$$Mop_{try(t_n,3)} = Mop(t_{n-1}) - 50 + 10$$

$$\vdots$$

-continued $$Mop_{try(t_n,j)} = Mop(t_{n-1}) - 50 + 5*(j-1)$$

$$\vdots$$

$$Mop_{try(t_n,20)} = Mop(t_{n-1}) - 50 + 95$$

However, the exact values used in the non-limiting examples set forth above are not required, and, in some alternative embodiments, one or more of N, the search step for Mop, and the search step for NMop may be different.

In some embodiments, in updating on or more of the lag parameters, the transceiver 101 may apply an upper and lower boundary for NMop and Mop. For example, if NMop-$0.1<LB\_NMop$, $NMop_{try(t\_n,1)}$ may be $LB\_NMop$ instead (that is, $NMop_{try(t_n,1)}=LB\_NMop$). The same may apply to the upper boundary and Mop. In some non-limiting embodiments, one or more of the boundaries may be saved (e.g., in a sensor calibration file) as a percentage relative to the fixed lag parameters in that period.

In some embodiments, weights for up to a number of reference measurements (e.g., up to 10 SMBGs) in the buffer may be calculated as below:

$$\text{Weight}(t_{n-i}) = \exp\left(\frac{t_n - t_{n-i}}{weightTimeConstantSeconds}\right),$$

where i=0 to 9, and weightTimeConstantSeconds is a parameter in the calibration file. In some non-limiting embodiments, weightTimeConstantSeconds may be specified as $t_n$-$t_{n-1}$.

For each $NMop_{try}$ and $Mop_{try}$ combination, BG is calculated according to (1) and the residual and deviation are defined as below:

$$\text{Residual}(iNMop_{try}, jMop_{try}) =$$

$$\sqrt{\Sigma_{k=0}^{9}[\text{Weight}(t_{n-k}) * weightedMARD(t_{n-k})]^2},$$

where $k = 1$ to 9

$$\text{Deviation}(iNMop_{try}, jMop_{try}) =$$

$$\frac{|NMop_{try}(t_n, iNMop_{try}) - NMop(t_{n-1})|}{0.1} +$$

$$\frac{|Mop_{try}(t_n, jMop_{try}) - Mop(t_{n-1})|}{50}.$$

$$weightedMARD(t_n) =$$

$$\begin{cases} \frac{|BG(t_n) - FS(t_n)|}{FS(t_n)}, & \text{if } FS(t_n) \geq hypoglycemiaThresholdMgDl \\ \frac{|BG(t_n) - FS(t_n)|}{hypoglycemiaThresholdMgDl}, & \text{if } FS(t_n) < hypoglycemiaThresholdMgDl \end{cases}$$

, where FS is the reference measurement or calibration point (e.g., an SMBG measurement). In some non-limiting alternative embodiments, the equation above for Residual(iNMop_try,jMop_try) may additionally include a time domain weight $v(t_{n-k})$. See paragraphs 0099-0101 below for additional information regarding the time domain weight.

In some non-limiting embodiments, in the dynamic lag parameter update step 718, the transceiver 101 may find all the $NMop_{try}$ and $Mop_{try}$ combinations with a Residual within 105% (can change) of the minimal Residual, and select the NMop$_{try}$ and Mop$_{try}$ combination with the minimal Deviation as the updated lag parameters L$_2$ and L$_1$. The updated L$_2$ and L$_1$ may be saved in the calibration point memory (e.g., a circular buffer) and used for lag compensation until the next calibration point (i.e., until the next reference measurement RM1 is received in step 706 and stored in step 708).

In some embodiments, in the dynamic lag parameter update step 718, the transceiver 101 may use one or more of first and second methods to update the lag parameters L1 and L2 during first and second periods, respectively. In some non-limiting embodiments, the first method may be the ratio method. In some non-limiting embodiments, the second method may be the two parameter method. In some non-limiting embodiments, the ratio method may determine a value MF1 that describes the relationship between baseline fluorescence of the analyte indicator element 106 and a change in sensor opacity that occurs with hydration. In some embodiments, the ratio method may use MDDM to determine the parameter with the best fit and minimal divergence from the previous parameter.

In some non-limiting embodiments, in the dynamic lag parameter update step 718, the transceiver 101 may use the first and second methods to update the lag parameters L1 and L2 during first and second periods, respectively. For example, in some non-limiting embodiments, the transceiver 101 may use the first method to estimate the updated lag parameters during the first period and may use the second method to estimate the updated lag parameters during the second period. In some non-limiting embodiments, the first period may be the period from sensor insertion until a predetermined amount of time (such as, for example and without limitation, 10 days) has passed. In some alternative embodiments, the first period may be the period from sensor insertion until the time at which the second method becomes more accurate than the first method (e.g., as determined by comparing sensor measurements calculated using the first and second methods with received reference measurements). In some non-limiting embodiments, the second period may begin when the first period ends. In some non-limiting embodiments, the second period may continue until the end of sensor life, but this is not required. In some alternative embodiments, the second period may end after a predetermined amount of time, and the transceiver 101 may use a third method to estimate the updated lag parameters during a third period of time that begins when the second period ends.

In some alternative embodiments, in the dynamic lag parameter update step 718, the transceiver 101 may use the first and second methods simultaneously (instead of sequentially) to update the lag parameters L1 and L2. For example, in some alternative embodiments, the transceiver 101 may estimate (i) a first set of updated lag parameters using the first method and (ii) a second set of updated lag parameters using the second method. The transceiver 101 may calculate sensor measurements using both the first and second sets of updated lag parameters. The transceiver 101 may evaluate the calculated sensor measurements for accuracy by comparing them to one or more reference measurements (e.g., one or more self-monitoring blood glucose (SHBG) measurements such as, for example and without limitation, one or more finger-stick measurements). The transceiver 101 may select the more accurate calculated sensor measurements for display to the user.

In some embodiments, as shown in FIG. 9, the process 700 may proceed from dynamic lag parameter update step 718 to a calibration step 710.

In some embodiments, the calibration process 700 may include a step 710 in which the transceiver 101 may calibrate the conversion function used to calculate blood analyte measurements from sensor data. In some non-limiting embodiments, the transceiver 101 may calibrate the conversion function using one or more of the calibration points stored in the calibration point memory. In some embodiments, the one or more calibration points used to calibrate the conversion function may include the reference measurement RM1. In some non-limiting embodiments, the transceiver 101 may assign weights to the one or more calibration points.

In some non-limiting embodiments, in step 710, the transceiver 101 may assign weights to the one or more calibration points according to, for example and without limitation, a weighted average cost function. In some non-limiting embodiments, the weighted average cost function may, for example and without limitation, have the following form:

$$\text{cost function} = \sqrt{\sum_{i=-(N-1)}^{0} (w_i * v_i * \text{Error}(\theta)_i)^2}$$

In some embodiments, in the weighted average cost function set forth above, $\theta$ may be one or more calibration parameters, $w_i$ may be a time domain weight for the calibration point, $v_i$ may be an analyte concentration domain weight for the calibration point, and Error$(\theta)_i$ may be an accuracy metric between the SMBG calibration points and the calculated sensor analyte concentration (SM1).

In some embodiments, the time domain weight, $w_i$, may be calculated in the following manner:

$$w_i = \exp\left(\frac{t_i - t_0}{\lambda}\right), i = -(N-1), -(N-2), \ldots 0$$

In these embodiments, $t_0$ may be the time stamp of the current calibration point, $t_{-(N-1)}, t_{-(N-2)}, \ldots, t_{-1}$ may be time stamps for previous N−1 calibration points, and $\lambda$ may be a relative time difference between the current and the previous calibration points, $t_0$-$t_{-1}$. In some embodiments, $\lambda$ may be a constant such as, for example and without limitation, 111328 seconds. In some embodiments, N may be a constant such as, for example and without limitation, 10. However, these specific values of $\lambda$ and N are not required, and, in some alternative embodiments, different values may be used for one or more of $\lambda$ and N.

In some non-limiting embodiments, the transceiver 101 may assign weights based on the age of the calibration points with less weight being given to older calibration points (e.g., in accordance with the weighted average cost function described above). However, this is not required, and the transceiver 101 may assign weights to the calibration points based on other computational or analytical methodologies.

In some embodiments, the calibration step 710 may include pairing one or more of the calibration points stored in the calibration point memory, which may include the reference measurement RM1, with one or more of the sensor measurements SM1 calculated in step 704. In some embodiments, the transceiver 101 may pair a calibration point with the sensor measurement SM1 having a time stamp closest to the time stamp of the calibration point. In some alternative embodiments, the transceiver 101 may pair a calibration point with an interpolated sensor measurement value if no sensor measurement SM1 has a time stamp that exactly matches the time stamp of the calibration point. That is, in some alternative embodiments, if the time stamp of the calibration point is in-between the time stamps of the sensor measurements SM1, the transceiver may pair the calibration point with an interpolated sensor measurement value. In some non-limiting embodiments, the transceiver 101 may use a sub-set or all of the sensor measurements SM1 and their time stamps to interpolate a sensor measurement value corresponding to the time stamp for the reference measurement RM1. In some non-limiting embodiments, the interpolation may be, for example and without limitation, linear interpolation, polynomial interpolation, or spline interpolation.

In some embodiments, the calibration process 700 may proceed from step 710 to step 702, and the transceiver 101 may use the updated conversion function to calculate blood analyte measurements from subsequent sensor data.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although the invention is described above in the context of an analyte monitoring system that calculates blood analyte levels indirectly using measurements of analyte levels in interstitial fluid, the invention is applicable to any monitoring system that calculates levels in a first medium using measurements of levels in a second medium.

What is claimed is:

1. A method of calculating an analyte level in a first medium using one or more measurements of an analyte level in a second medium, the method comprising:
   receiving first sensor data from an analyte sensor;
   calculating a first analyte level in the second medium using at least the first sensor data;
   calculating a first analyte level rate of change using at least the first analyte level in the second medium;
   calculating a first analyte level in the first medium using at least the first analyte level in the second medium, the first analyte level rate of change, and one or more lag parameters;
   determining that the one or more lag parameters should be updated;
   updating the one or more lag parameters;
   receiving second sensor data from the analyte sensor;
   calculating a second analyte level in the second medium using at least the second sensor data;
   calculating a second analyte level rate of change using at least the second analyte level in the second medium; and
   calculating a second analyte level in the first medium using at least the second analyte level in the second medium, the second analyte level rate of change, and the updated one or more lag parameters;
   wherein the one or more lag parameters include one or more of an analyte diffusion rate and an analyte consumption rate.

2. The method of claim 1, wherein the first medium is blood, and the second medium is interstitial fluid.

3. The method of claim 1, further comprising determining whether to dynamically update one or more of the lag parameters.

4. The method of claim 3, further comprising dynamically updating one or more of the lag parameters.

5. The method of claim 4, wherein dynamically updating one or more of the lag parameters comprises using a minimum deviation divergence method.

6. The method of claim 1, further comprising dynamically updating one or more of the lag parameters.

7. A method of calculating an analyte level in a first medium using one or more measurements of an analyte level in a second medium, the method comprising:
   receiving first sensor data from an analyte sensor;
   calculating a first analyte level in the second medium using at least the first sensor data;
   calculating a first analyte level rate of change using at least the first analyte level in the second medium;
   calculating a first analyte level in the first medium using at least the first analyte level in the second medium, the first analyte level rate of change, and one or more lag parameters;
   determining that the one or more lag parameters should be updated, wherein determining that the one or more lag parameters should be updated comprises determining that a period of time has passed since the one or more of the lag parameters have been updated;
   updating the one or more lag parameters;
   receiving second sensor data from the analyte sensor;
   calculating a second analyte level in the second medium using at least the second sensor data;
   calculating a second analyte level rate of change using at least the second analyte level in the second medium; and
   calculating a second analyte level in the first medium using at least the second analyte level in the second medium, the second analyte level rate of change, and the updated one or more lag parameters.

8. The method of claim 7, wherein the one or more lag parameters include one or more of an analyte diffusion rate and an analyte consumption rate.

9. A method of calculating an analyte level in a first medium using one or more measurements of an analyte level in a second medium, the method comprising:
   receiving first sensor data from an analyte sensor;
   calculating a first analyte level in the second medium using at least the first sensor data;
   calculating a first analyte level rate of change using at least the first analyte level in the second medium;
   calculating a first analyte level in the first medium using at least the first analyte level in the second medium, the first analyte level rate of change, and one or more lag parameters, wherein calculating the first analyte level in the first medium comprises employing an asymmetrical lag methodology;
   determining that the one or more lag parameters should be updated;
   updating the one or more lag parameters;
   receiving second sensor data from the analyte sensor;
   calculating a second analyte level in the second medium using at least the second sensor data;
   calculating a second analyte level rate of change using at least the second analyte level in the second medium; and
   calculating a second analyte level in the first medium using at least the second analyte level in the second medium, the second analyte level rate of change, and the updated one or more lag parameters.

10. The method of claim 9, wherein the asymmetrical lag approach decelerates a rate of change of falling analyte levels during a low blood analyte event and accelerates a rate of change of increasing analyte levels during recovery from the low blood analyte event.

11. A method of calculating an analyte level in a first medium using one or more measurements of an analyte level in a second medium, the method comprising:
receiving first sensor data from an analyte sensor;
calculating a first analyte level in the second medium using at least the first sensor data;
calculating a first analyte level rate of change using at least the first analyte level in the second medium;
calculating a first analyte level in the first medium using at least the first analyte level in the second medium, the first analyte level rate of change, and one or more lag parameters;
determining that the one or more lag parameters should be updated;
updating the one or more lag parameters, wherein updating the one or more lag parameters comprises using one or more of a first method and a second method to estimate one or more updated lag parameters;
receiving second sensor data from the analyte sensor;
calculating a second analyte level in the second medium using at least the second sensor data;
calculating a second analyte level rate of change using at least the second analyte level in the second medium; and
calculating a second analyte level in the first medium using at least the second analyte level in the second medium, the second analyte level rate of change, and the updated one or more lag parameters.

12. The method of claim 11, wherein the first method is a ratio method.

13. The method of claim 11, wherein the second method is a two-parameter method.

14. The method of claim 11, wherein updating one or more lag parameters comprises using the first method during a first period and using the second method during a second period.

15. The method of claim 11, wherein updating one or more lag parameters comprises using both the first and second methods.

16. The method of claim 15, wherein using both the first and second methods comprises:
using the first method to estimate a first set of updated lag parameters;
using the second method to estimate a second set of updated lag parameters;
using the first set of updated lag parameters to calculate one or more first sensor measurements;
using the second set of updated lag parameters to calculate one or more second sensor measurements;
evaluating the one or more first sensor measurements and the one or more second sensor measurements by comparing the one or more first sensor measurements and the one or more second sensor measurements to one or more reference measurements; and
selecting the more accurate of (a) the one or more first sensor measurements and (b) the one or more second sensor measurements for display to a user.

17. An analyte monitoring system comprising:
an analyte sensor including an indicator element that exhibits one or more detectable properties based on a concentration of an analyte in proximity to the indicator element; and
a transceiver configured to:
receive first sensor data from the analyte sensor;
calculate a first analyte level in the second medium using at least the first sensor data;
calculate a first analyte level rate of change using at least the first analyte level in the second medium;
calculate a first analyte level in the first medium using at least the first analyte level in the second medium, the first analyte level rate of change, and one or more lag parameters;
determine that the one or more lag parameters should be updated;
update the one or more lag parameters;
receive second sensor data from the analyte sensor;
calculate a second analyte level in the second medium using at least the second sensor data;
calculate a second analyte level rate of change using at least the second analyte level in the second medium;
calculate a second analyte level in the first medium using at least the second analyte level in the second medium, the second analyte level rate of change, and the updated one or more lag parameters;
wherein the one or more lag parameters include one or more of an analyte diffusion rate and an analyte consumption rate.

18. The analyte monitoring system of claim 17, wherein the first medium is blood, and the second medium is interstitial fluid.

19. The analyte monitoring system of claim 17, wherein the transceiver is further configured to determine whether to dynamically update one or more of the lag parameters.

20. The analyte monitoring system of claim 19, wherein the transceiver is further configured to dynamically update one or more of the lag parameters.

21. The analyte monitoring system of claim 20, wherein dynamically updating one or more of the lag parameters comprises using a minimum deviation divergence method.

22. The analyte monitoring system of claim 17, wherein the transceiver is further configured to dynamically update one or more of the lag parameters.

23. An analyte monitoring system comprising:
an analyte sensor including an indicator element that exhibits one or more detectable properties based on a concentration of an analyte in proximity to the indicator element; and
a transceiver configured to:
receive first sensor data from the analyte sensor;
calculate a first analyte level in the second medium using at least the first sensor data;
calculate a first analyte level rate of change using at least the first analyte level in the second medium;
calculate a first analyte level in the first medium using at least the first analyte level in the second medium, the first analyte level rate of change, and one or more lag parameters;
determine that the one or more lag parameters should be updated, wherein determining that the one or more lag parameters should be updated comprises determining that a period of time has passed since the one or more of the lag parameters have been updated;
update the one or more lag parameters;
receive second sensor data from the analyte sensor;
calculate a second analyte level in the second medium using at least the second sensor data;
calculate a second analyte level rate of change using at least the second analyte level in the second medium; and calculate a second analyte level in the first medium using at least the second analyte level in the second medium, the second analyte level rate of change, and the updated one or more lag parameters.

24. The analyte monitoring system of claim 23, wherein the one or more lag parameters include one or more of an analyte diffusion rate and an analyte consumption rate.

25. An analyte monitoring system comprising:
an analyte sensor including an indicator element that exhibits one or more detectable properties based on a concentration of an analyte in proximity to the indicator element; and
a transceiver configured to:
receive first sensor data from the analyte sensor;
calculate a first analyte level in the second medium using at least the first sensor data;
calculate a first analyte level rate of change using at least the first analyte level in the second medium;
calculate a first analyte level in the first medium using at least the first analyte level in the second medium, the first analyte level rate of change, and one or more lag parameters, wherein calculating the first analyte level in the first medium comprises employing an asymmetrical lag methodology;
determine that the one or more lag parameters should be updated;
update the one or more lag parameters;
receive second sensor data from the analyte sensor;
calculate a second analyte level in the second medium using at least the second sensor data;
calculate a second analyte level rate of change using at least the second analyte level in the second medium; and
calculate a second analyte level in the first medium using at least the second analyte level in the second medium, the second analyte level rate of change, and the updated one or more lag parameters.

26. The analyte monitoring system of claim 25, wherein the asymmetrical lag approach decelerates a rate of change of falling analyte levels during a low blood analyte event and accelerates a rate of change of increasing analyte levels during recovery from the low blood analyte event.

27. An analyte monitoring system comprising:
an analyte sensor including an indicator element that exhibits one or more detectable properties based on a concentration of an analyte in proximity to the indicator element; and
a transceiver configured to:
receive first sensor data from the analyte sensor;
calculate a first analyte level in the second medium using at least the first sensor data;
calculate a first analyte level rate of change using at least the first analyte level in the second medium;
calculate a first analyte level in the first medium using at least the first analyte level in the second medium, the first analyte level rate of change, and one or more lag parameters;
determine that the one or more lag parameters should be updated;
update the one or more lag parameters, wherein updating the one or more lag parameters comprises using one or more of a first method and a second method to estimate one or more updated lag parameters;
receive second sensor data from the analyte sensor;
calculate a second analyte level in the second medium using at least the second sensor data;
calculate a second analyte level rate of change using at least the second analyte level in the second medium; and
calculate a second analyte level in the first medium using at least the second analyte level in the second medium, the second analyte level rate of change, and the updated one or more lag parameters.

28. The analyte monitoring system of claim 27, wherein the first method is a ratio method.

29. The analyte monitoring system of claim 27, wherein the second method is a two-parameter method.

30. The analyte monitoring system of claim 27, wherein updating one or more lag parameters comprises using the first method during a first period and using the second method during a second period.

31. The analyte monitoring system of claim 27, wherein updating one or more lag parameters comprises using both the first and second methods.

32. The analyte monitoring system of claim 31, wherein using both the first and second methods comprises:
using the first method to estimate a first set of updated lag parameters;
using the second method to estimate a second set of updated lag parameters;
using the first set of updated lag parameters to calculate one or more first sensor measurements;
using the second set of updated lag parameters to calculate one or more second sensor measurements;
evaluating the one or more first sensor measurements and the one or more second sensor measurements by comparing the one or more first sensor measurements and the one or more second sensor measurements to one or more reference measurements; and
selecting the more accurate of (a) the one or more first sensor measurements and (b) the one or more second sensor measurements for display to a user.

33. A method of calculating an analyte level in a first medium using one or more measurements of an analyte level in a second medium, the method comprising:
receiving first sensor data from an analyte sensor;
calculating a first analyte level in the second medium using at least the first sensor data;
calculating a first analyte level rate of change using at least the first analyte level in the second medium;
calculating a first analyte level in the first medium using at least the first analyte level in the second medium, the first analyte level rate of change, and a first set of one or more lag parameters;
calculating a second analyte level in the first medium using at least the first analyte level in the second medium, the first analyte level rate of change, and a second set of one or more lag parameters;
comparing the first analyte level in the first medium to at least a reference measurement;
comparing the second analyte level in the first medium to at least the reference measurement; and
selecting whichever of the first analyte level in the first medium and the second analyte level in the first medium is closer to the reference measurement for display to a user.

34. An analyte monitoring system comprising:
an analyte sensor including an indicator element that exhibits one or more detectable properties based on a concentration of an analyte in proximity to the indicator element; and
a transceiver configured to:
receive first sensor data from the analyte sensor;

calculate a first analyte level in the second medium using at least the first sensor data;
calculate a first analyte level rate of change using at least the first analyte level in the second medium;
calculate a first analyte level in the first medium using at least the first analyte level in the second medium, the first analyte level rate of change, and a first set of one or more lag parameters;
calculate a second analyte level in the first medium using at least the first analyte level in the second medium, the first analyte level rate of change, and a second set of one or more lag parameters;
compare the first analyte level in the first medium to at least a reference measurement;
compare the second analyte level in the first medium to at least the reference measurement; and
select whichever of the first analyte level in the first medium and the second analyte level in the first medium is closer to the reference measurement for display to a user.

* * * * *